United States Patent
Anton et al.

(10) Patent No.: US 10,011,832 B2
(45) Date of Patent: Jul. 3, 2018

(54) SIRNA AND THEIR USE IN METHODS AND COMPOSITIONS FOR THE TREATMENT AND/OR PREVENTION OF EYE CONDITIONS

(75) Inventors: Ana Isabel Jimenez Anton, Madrid (ES); Victoria Gonzalez Fajardo, Madrid (ES); Veronica Ruz Palomar, Madrid (ES)

(73) Assignee: SYLENTIS SAU, Madrid (ES)

(*) Notice: Subject to any disclaimer, the term of this patent is extended or adjusted under 35 U.S.C. 154(b) by 0 days.

(21) Appl. No.: 14/425,466

(22) PCT Filed: Sep. 5, 2012

(86) PCT No.: PCT/GB2012/052177
§ 371 (c)(1),
(2), (4) Date: Mar. 3, 2015

(87) PCT Pub. No.: WO2014/037686
PCT Pub. Date: Mar. 13, 2014

(65) Prior Publication Data
US 2015/0259677 A1   Sep. 17, 2015

(51) Int. Cl.
| | |
|---|---|
| *A61K 48/00* | (2006.01) |
| *C07H 21/02* | (2006.01) |
| *C07H 21/04* | (2006.01) |
| *C12N 15/11* | (2006.01) |
| *C12N 15/113* | (2010.01) |

(52) U.S. Cl.
CPC ........ *C12N 15/113* (2013.01); *C12N 15/1138* (2013.01); *C12N 2310/14* (2013.01); *C12N 2310/50* (2013.01); *C12N 2320/32* (2013.01)

(58) Field of Classification Search
CPC ............ A61K 31/7088; C12N 15/1138; C12N 2310/14
USPC ............................................ 514/44; 536/24.5
See application file for complete search history.

(56) References Cited

U.S. PATENT DOCUMENTS

| 4,343,794 A | 8/1982 | Podos et al. |
|---|---|---|
| 4,617,299 A | 10/1986 | Knepper |
| 4,652,586 A | 3/1987 | Nathanson |
| 4,757,089 A | 7/1988 | Epstein |
| 4,812,448 A | 3/1989 | Knepper |
| 5,075,323 A | 12/1991 | Fain et al. |
| 5,242,943 A | 9/1993 | Louis et al. |

(Continued)

FOREIGN PATENT DOCUMENTS

| AU | 2005276245 | 3/2006 |
|---|---|---|
| EP | 1 527 176 | 1/2007 |

(Continued)

OTHER PUBLICATIONS

What Are the Symptoms of Glaucoma? Written by Kierstan Boyd (downloaded from https://www.aao.org/eye-health/diseases/glaucoma-symptoms on Oct. 31, 2017).*

(Continued)

*Primary Examiner* — Terra C Gibbs
(74) *Attorney, Agent, or Firm* — Margaret B. Brivanlou; Kenneth H. Sonnenfeld; King & Spalding LLP

(57) ABSTRACT

The present invention relates to methods, compositions and dosages that decrease IOP of the eye, comprising a 19 nucleotide double-stranded RNA molecule.

11 Claims, 13 Drawing Sheets

(56) References Cited

U.S. PATENT DOCUMENTS

| | | | |
|---|---|---|---|
| 5,260,059 | A | 11/1993 | Acott et al. |
| 5,464,866 | A | 11/1995 | Clark et al. |
| 5,545,626 | A | 8/1996 | Stein et al. |
| 5,585,401 | A | 12/1996 | Brandt et al. |
| 6,365,576 | B1 | 4/2002 | Carr |
| 6,372,249 | B1 | 4/2002 | Smith et al. |
| 6,489,307 | B1 | 12/2002 | Phillips et al. |
| 7,176,304 | B2 | 2/2007 | McSwiggen et al. |
| 7,294,504 | B1 | 11/2007 | Wang |
| 7,462,602 | B2 | 12/2008 | Schultz et al. |
| 7,521,431 | B2 | 4/2009 | Reich et al. |
| 7,579,457 | B2 | 8/2009 | Khvorova et al. |
| 7,592,324 | B2 | 9/2009 | Shepard et al. |
| 7,592,325 | B2 | 9/2009 | Jimenez et al. |
| 7,618,814 | B2 | 11/2009 | Bentwich |
| 7,655,789 | B2 | 2/2010 | Khvorova et al. |
| 7,687,665 | B2 | 3/2010 | Yao et al. |
| 7,691,997 | B2 | 4/2010 | Khvorova et al. |
| 7,700,575 | B2 | 4/2010 | Andrew et al. |
| 8,030,284 | B2 | 10/2011 | Jimenez et al. |
| 8,090,542 | B2 | 1/2012 | Khvorova et al. |
| 2002/0055536 | A1 | 5/2002 | DeWitte et al. |
| 2002/0114784 | A1 | 8/2002 | Li et al. |
| 2002/0165158 | A1 | 11/2002 | King |
| 2004/0029275 | A1 | 2/2004 | Brown et al. |
| 2004/0115641 | A1 | 6/2004 | Cowsert et al. |
| 2004/0167090 | A1 | 8/2004 | Monahan et al. |
| 2004/0198640 | A1 | 10/2004 | Leake et al. |
| 2004/0209832 | A1 | 10/2004 | McSwiggen et al. |
| 2004/0224405 | A1 | 11/2004 | Leake et al. |
| 2004/0235031 | A1 | 11/2004 | Schultz et al. |
| 2004/0259247 | A1 | 12/2004 | Tuschl et al. |
| 2004/0266707 | A1 | 12/2004 | Leake et al. |
| 2005/0020521 | A1 | 1/2005 | Rana |
| 2005/0171039 | A1 | 8/2005 | McSwiggen et al. |
| 2005/0208658 | A1 | 9/2005 | Castonguay |
| 2005/0255487 | A1 | 11/2005 | Khvorova et al. |
| 2006/0058266 | A1 | 3/2006 | Manoharan et al. |
| 2006/0094032 | A1 | 5/2006 | Fougerolles et al. |
| 2006/0122136 | A1 | 6/2006 | Schubert |
| 2006/0172963 | A1 | 8/2006 | Shepard et al. |
| 2006/0172965 | A1 | 8/2006 | Shepard et al. |
| 2006/0257851 | A1 | 11/2006 | Bentwich |
| 2007/0049543 | A1 | 3/2007 | McSwiggen et al. |
| 2007/0050146 | A1 | 3/2007 | Bentwich et al. |
| 2007/0093435 | A1 | 4/2007 | Andrews et al. |
| 2007/0167384 | A1 | 7/2007 | Leake et al. |
| 2009/0326044 | A1 | 12/2009 | Shepard et al. |
| 2012/0094374 | A1 | 4/2012 | Bentwich et al. |

FOREIGN PATENT DOCUMENTS

| | | |
|---|---|---|
| GB | 2406568 | 4/2005 |
| WO | WO 2003/057840 | 7/2003 |
| WO | WO 2003/059267 | 7/2003 |
| WO | WO 2003/070744 | 8/2003 |
| WO | WO 2003/087367 | 10/2003 |
| WO | WO 2003/092584 | 11/2003 |
| WO | WO 2004/009794 | 1/2004 |
| WO | WO 2004/009796 | 1/2004 |
| WO | WO 2004/029212 | 4/2004 |
| WO | WO 2004/042024 | 5/2004 |
| WO | WO 2005/032493 | 4/2005 |
| WO | WO 2005/044976 | 5/2005 |
| WO | WO 2005/045037 | 5/2005 |
| WO | WO 2005/076998 | 8/2005 |
| WO | WO 2005/079815 | 9/2005 |
| WO | WO 2006/021817 | 3/2006 |
| WO | WO 2006/083945 | 8/2006 |
| WO | WO 2006/084217 | 8/2006 |
| WO | WO 2006/099353 | 9/2006 |
| WO | WO 2008/024983 | 2/2008 |
| WO | WO 2014/037686 | 3/2014 |

OTHER PUBLICATIONS

Burnett et al., "Current Progress of siRNA/shRNA Therapeutics in Clinical Trials," Biotechnology Journal, vol. 6, No. 9, pp. 1130-1146, Jul. 2011.

Fattal et al., "Ocular Delivery of Nucleic Acids: Antisense Oligonucleotides, Aptamers and siRNA," Advanced Drug Delivery Reviews, vol. 58, No. 11, pp. 1203-1223, Sep. 2006.

Martin-Gil et al., "Silencing of P2Y2 Receptors Reduces Intraocular Pressure in New Zealand Rabbits," British Journal of Pharmacology, vol. 165, pp. 1163-1172, Feb. 2012.

Mediero et al., "New Treatments for Ocular Hypertension," Autonomic Neuroscience: Basic and Clinical, vol. 147, No. 1-2, pp. 14-19, May 2009.

Pintor, "Silencing Beta2-Adrenergic Receptors Reduces Intraocular Pressure: A New Approach for Glaucoma Therapy," Anales De La Real Academia Nacional De Farmacia, vol. 78, No. 2, pp. 230-240, Jun. 2012.

Pintor et al., "SiRNA in the Treatment of Ocular Hypertension Targeting Alpha and Beta Adrenoceptors," Invest. Ophthalmol. Vis. Sci., vol. 47, p. 403, 2006.

Ruz et al., "Phase I Study with a New siRNA: SYL040012, Tolerance and Effect on Intraocular Pressure," Investigative Ophthalmology & Visual Science, vol. 52, pp. 223, May 2011.

Zhang et al., "Ophthalmic Drug Discovery: Novel Targets and Mechanisms for Retinal Diseases and Glaucoma," Nature Reviews Drug Discovery, vol. 11, No. 7, pp. 541-559, Jun. 2012.

Sylentis SAU, International Search Report for PCT/GB2012/052177, 5 pages, dated May 16, 2013.

Abrams et al., "Comparison of Three Tonometers for Measuring Intraocular Pressure in Rabbits," Invest Ophthalmol Vis Sci. Apr. 1996, 37(5):940-944.

Achenbach et al., Oligonucleotide-Based Knockdown Technologies: Antisense Versus RNA Interference, ChemBioChem., 4, pp. 928-935, 2003.

"Acuity has New Approach to AMD, Its Drug is Designed to Shut Down VEGF Production" Ophthalmology Management, Apr. 1, 2004, pp. 1-4—cited in AU opposition.

The Agis Investigators, "The Advanced Glaucoma Intervention Study (AGIS): 7. The Relationship Between Control of Intraocular Pressure and Visual Field Deterioration," Am. J. Ophthalmol., 130, pp. 429-440, 2000—Cited in AU Opposition.

Akashi et al., "Suppression of Gene Expression by RNA Interference in Cultured Plant Cells," Antisense Nucleic Acid Drug Dev, 2001, 11(6):359-367.

Amaratunga et al., "Inhibition of Kinesin Synthesis and Rapid Anterograde Axonal Transport in Vivo by an Antisense Oligonucleotide," The Journal of Biological Chemistry, 268(23) pp. 17427-17430, Aug. 15, 1993.

Ambati et al., "Transscleral Delivery of Bioactive Protein to the Choroid and Retina," Investigative Ophthalmology & Visual Science, vol. 41, No. 5, pp. 1186-1191, Apr. 2000.

Ambion, "The Basics: RNase Control," printout from website <<http://web.archive.org/web/20041207234247>>, dated 2004, retrieved on Sep. 17, 2009.

Ambion, Tech Notes 10(4) and siRNA Target Finder (http://www.ambion.com/techlib/misc/siRNA_finder.html, available to the public) retrieved on May 1, 2008, siRNA target hit for SEQ ID No. 139 included.

Amended Statement of Grounds and Particulars filed on Jun. 5, 2012 (amending original Grounds filed on Dec. 2, 2010), from opponents in Opposition by Alcon Research, Ltd. against Australian Patent Application No. 2005276245 in the name of Sylentis SAU.

Andrieu-Soler C., et al "Ocular gene therapy: A review of nonviral strategies," Molecular Vision, 12:1334-47, 2006.

Aravin et al., "Role of Double-Stranded RNA in Eukaryotic Gene Silencing," Mol. Biol. (Mosk.), 36(2), pp. 240-251, Mar.-Apr. 2002, Abstract Only.

Banan et al., "The Ins and Outs of RNAi in Mammalian Cells," Current Pharmaceutical Biotechnology, 5, pp. 441-450, 2004.

(56) References Cited

OTHER PUBLICATIONS

Banerjee et al., "Control of Developmental Timing by Small Temporal RNAs: a Paradigm for RNA-mediated Regulation of Gene Expression," Bioessays, 2002, 24(2):119-129.
Barar J. et al., "Ocular novel drug delivery impacts of membranes and barriers," Expert Opin. Drug Deliv., 5(5): 567-81, 2008.
Bass, "The Short Answer," Nature, vol. 411, pp. 428-429, 2001.
Bhattacharya et al., "Cochlin Deposits in the Trabecular Meshwork of the Glaucomatous DBA/2J mouse," Exp Eye Res., May 2005 80(5):741-744.
Bhattacharya et al., "Proteomics Reveal Cochlin Deposits Associated with Glaucomatous Trabecular Meshwork," J. Biol. Chem., Feb. 2005b, 18;280(7):6080-6084, Epub Dec. 3, 2004.
Bill, "Movement of Albumin and Dextran," Arch. Opthal., vol. 74, pp. 248-252, Aug. 1965.
Borrás, "Gene Expression in the Trabecular Meshwork and the Influence of Intraocular Pressure," *Progress in Retinal and Eye Research*, 22, 435-463, 2003.
Bosher et al., "RNA Interference: Genetic Wand and Genetic Watchdog." Nat Cell Biol, 2000, 2(2):E31-6.
Braasch et al., "Novel Antisense and Peptide Nucleic Acid Strategies for Controlling Gene Expression," Biochemistry, 2002, 41(14):4503-4510.
Brummelkamp et al., "A System for Stable Expression of Short Interfering RNAs in Mammalian Cells," Science, American Association for the Advancement of Science, 2002, 296(5567):550-553.
Busch et al., "Adenylyl Cyclase in Human and Bovine Trabecular Meshwork," Investigative Ophthalmology & Visual Science, 34(10), pp. 3028-3034, Sep. 1993.
Bunce et al., "Associations between the deletion polymorphism of the angiotensin 1-converting enzyme gene and ocular signs of primary open-angle glaucoma," Graefes Arch Clin Exp Ophthalmol., Apr. 2005 243(4):294-299. Epub Oct. 13, 2004.
Caballero et al., "Inefficient Processing of an Olfactomedin-Deficient Myocilin Mutant: Potential Physiological Relevance to Glaucoma," *Biochemical and Biophysical Research Communications*, 282, 662-670, 2001.
Caplen et al., "Specific inhibition of Gene Expression by Small Double Stranded RNAs in Invertebrate and Vertebrate Systems," Proc. Natl. Acad. Sci. USA, 2001,98: 9742-9747.
Cho et al., "Small Interfering RNA-Induced TLR3 Activation Inhibits Blood and Lymphatic Vessel Growth," PNAS, pp. 1-6, Dec. 5, 2008.
Chudgar et al., "Elevated Intraocular Pressure and Mechanical Stress Increase Connective Tissue Growth Factos Expression in the Trabecular Meshwork," Invest Ophthalmol Vis Sci, 45, E-Abstract 4433, 2004.
Clark et al., "Opthalamic Drug Discovery," Nature Reviews Drug Discover, pp. 448-459, 2003.
Comes N. and Borrás T, "Functional delivery of synthetic naked siRNA to the human trabecular meshwork in perfused organ cultures," Molec. Vision, 13: 1363-74, 2007.
Costagliola et al., "Effect of Oral Losartan Potassium Administration on Intraocular Pressure in Normotensive and Glaucomatous Human Subjects," Exp Eye Res., Aug. 2000, 71(2):167-171.
Costagliola et al., "Effect of Oral Captopril (SQ 14225) on Intraocular Pressure in Man," Eur. J. Opthalmol, Jan. 1995, 5(1):19-25.
Crooke et al., "Nucleotides in Ocular Secretions: Their Role in Ocular Physiology," Pharmacology & Therapeutics, 119, pp. 55-73, 2008.
Cullinane et al., "Renin-angiotensin System Expression and Secretory Function in Cultured human Ciliary Cody Nonpigmented Epithelium," Br J Ophthalmol. Jun. 2002, 86(6):676-83.
Davson H, "The Aqueous Humour and The Intraocular Pressure," Davson's Physiology of the Eye, 5th edition, Pergamon Press, pp. 3-95, 1990.
Dejneka NS., et al., "Ocular Biodistribution of Bevasiranib Following a Single Intravitreal Injection to Rabbit Eyes," Molecular Vision, 14:997-1005, 2008.
Denkert et al., "Induction of G0/G1 Cell Cycle Arrest in Ovarian Carcinoma Cells by the Ant-Inflammatory Drug NS-398, but not by COX-2-Specific RNA Interference," Oncogene, 2003, 22:8653-8661.
Diffen, DNA vs. RNA—Difference and Comparison, retrieved from <<http://www.diffen.com/difference/Dna_vs_Rna>> on May 21, 2009.
Dinslage et al., "Intraocular Pressure in Rabbits by Telemetry II: Effects of Animal Handling and Drugs," Invest. Ophthalmol Vis Sci., vol. 39(12), pp. 2485-2489, 1998.
Diskin et al., "Detection of Differentially Expressed Glycogenes in Trabecular Meshwork of Eyes with Primary Open-Angle Glaucoma," Investigative Opthalmology & Visual Science, Apr. 2006, 47(4):1491-1499.
Dos Santos ALG., et al "Intraocular Delivery of Oligonucleotides," Current Pharmaceutical Biotechnology, 6:7-15, 2005.
Elabashir et al., "Duplexes of 21-Nucleotide RNAs mediate RNA interference in Cultured Mammalian Cells," Nature, May 24, 2001, 411(6836):494-498.
Elbashir et al., "Functional Anatomy of siRNAs for Mediating Efficient RNAi in *Drosophila Melanogaster* Embryo Lysate," EMBO Journal, vol. 20, No. 23, pp. 6877-6888, 2001.
Elbashir et al., "RNA Interference is Mediated by 21- and 22-Nucleotide RNAs," Genes Dev, 2001, 15(2):188-200.
Elena et al., "Autoradiographic Localization of Beta-Adrenergic Receptors in Rabbit Eye," Investigative Ophthalmology & Visual Science, 28, pp. 1436-1441, Aug. 1987.
Epstein et al., "*Effect of Iodoacetamide Perfusion on Outflow Facility and Metabolism of the Trabecular Meshwork*," Invest. Ophthalmol. Vis. Sci., 625-631, May 1981.
Fattal et al., "Ocular Delivery of Nucleic Acids: Antisense Oligonucleotides, Aptamers and siRNA," Advanced Drug Delivery Reviews, 2006, 58:1203-1223.
Fire et al., "Potent and Specific Genetic Interference by Double Stranded RNA in a Caenorhabditis Elegans," Nature, 1998, 391(6669):806-11.
Freier et al., "The Ups and Downs of Nucleic Acid Duplex Stability: Structure-Stability Studies on Chemically-Modified DNA:RNA Duplexes," Nucleic Acids Research, 25(22), pp. 4429-4443, 1997.
Fuchshofer et al., "The Effect of TGF-β2 on Human Trabecular Meshwork Extracellular Proteolytic System," Experimental Eye Research, 77, pp. 757-765, 2003.
Ganesh Prasanna, Ph.D., Resume, 12 pages, May 18, 2012.
Statutory Declaration of Ganesh Prasanna, 19 pages, Jun. 1, 2012.
Ge et al., "RNA Interference of Influenza Virus Production by Directly Targeting mRNA for Degradation and Indirectly Inhibiting all Viral RNA Transcription," Proc Natl Acad Sci USA., 2003, 100(5):2718-2723.
Ghate D. and Edelhauser H.F., "Barriers to glaucoma drug delivery," *J. Glaucoma*, 17(2), 147-56, 2008.
Gil et al., "Induction of Apoptosis by the dsRNA-dependent Protein Kinase (PKR): Mechanism of Action," Apoptosis, 2000, 5(2):107-114.
Gonzalez et al., "Genes Upregulated in the Human Trabecular Meshwork in Response to Elevated Intraocular Pressure," Investigative Opthalmology & Visual Science, Feb. 2000, 41(2):352-361.
Grosshans et al., "Micro-RNAs: Small is Plentiful," J Cell Bioi, 2002, 156(1):17-21.
Hammond et al., "Post-Transcriptional Gene Silencing by Double-Standed RNA," Nature, 2001, 2:110-119.
Hara et al., "Bunazosin, a Selective Alpha1-Adrenoceptor Antagonist, as an Anti-glaucoma Drug: Effects on Ocular Circulation and Retinal Neuronal Damage," Cardiovasc Drug Rev. 2005 Spring;23(1):43-56.
Hart WM, "Intraocular Pressure," Chapter 8, Adler's Physiology of the Eye: Clinical Application, Mosby-Year Book Inc., 9th edition, pp. 248-267, 1992.
Herkel et al., "Update on Topical Carbonic Anhydrase Inhibitors," Current Opinion in Ophthamology, Apr. 2001, 12(2):88-93.
Hogeboom et al., "Angiotensin Converting Enzyme Inhibiting Therapy is Associated with Lower Vitreous Vascular Endothelial Growth Factor Concentrations in Patients with Proliferative Diabetic Retinopathy," Diabetologia, vol. 45, pp. 203-209, 2002.

(56) References Cited

OTHER PUBLICATIONS

Horinouchi et al., "Pharmacological Evaluation of Ocular β-Adrenoceptors in Rabbit by Tissue Segment Binding Method," Life Sciences, 84, pp. 181-187, 2009.
Jens Kurreck, "Antisense Technologies," Eur. J. Biochem., 270, pp. 1628-1644, 2003.
Jens Kurreck, "Antisense and RNA Interference Approaches to Target Validation in Pain Research," Current Opinion in Drug Discovery & Development, 7(2), pp. 179-187, 2004.
Jiménez et al., "Efficacy of Topically Administered siRNAs in Glaucoma Treatment: In vivo Results in Hypertensive Model," Investigative Ophthalmology & Visual Science, 50, E-Abstract 4054, 2009.
Jiménez et al., "$Na^+/K^+$ATPase: A New Target for Treating Ocular Hypertension by RNAi," Investigative Ophthalmology & Visual Science, 48, E-Abstract 4809 2007.
Jiménez et al., "SYL04003: A New Therapeutic Candidate for Treating Ocular Hypertension using RNAi Technology," Investigative Ophthalmology & Visual Science, 49, E-Abstract 1643, 2008.
Jiménez et al., "SYL040012 A New siRNA-Based Treatment for Glaucoma: Pharmacokinetics and Mechanism of Action," Investigative Ophthalmology & Visual Science, 51, E-Abstract 176, 2010.
Kaplan et al., "Aqueous Humor Flow in Unilateral Carotid Stenosis," Journal of Glaucoma, 5, pp. 237-240, 1996.
Khaw et al., "Glaucoma-1: Diagnosis," BMJ, 2004a, 328:97-99.
Khaw et al., "Glaucoma-2: Treatment," BMJ, 2004, 328:156-158.
Kim et al., "Inhibition of Ocular Angiogenesis by Sirna Targeting Vascular Endothelial Growth Factor Pathway Genes Therapeutics Strategy for Herpetic Stromal Keratititis," American Journal of Pathology, Dec. 2004, 165(6):2177-285.
Krohn et al., "Transcorneal Flux of Topical Pilocarpine to the Human Aqueous," Am. J. Ophthalmol., 87(1), pp. 50-56, Jan. 1979, Abstract retrieved from <<http://www.ncbi.nlm.nih.gov/pubmed/434053>> on Nov. 9, 2009.
Krutzfeldt et al., "Silencing of microRNAs in vivo with 'Antagomirs'," Nature, 2005, 438(7068):685-689.
Kwon et al., "Primary Open-Angle Glaucoma," The New England Journal of Medicine, 360(11), pp. 1113-1124, Mar. 12, 2009.
Liao et al., "Expression of Cell Surface Transmembrane Carbonic Anhydrase Genes CA9 and CA12 in the Human Eye: Overexpression of CA12 (CAXII) in Glaucoma," J. Med. Genet, 40, 257-262, 2003.
Lograno et al., "Receptor-Responses in Fresh Human Ciliary Muscle," Br. J. Pharmac., 87, pp. 379-385, 1986.
Madsen, "Ocular Finding in 123 Patients with Proliferative Diabetic Retinopathy," Documenta Ophthalmologica, Advances in ophthalmology, May 14, 1971, 29(2):345-349.
Mahato et al., "Modulation of Gene Expression by Antisense and Antigene Oligodeoxynucleotides and Small Interfering RNA," Expert Opinion on Drug Delivery, Jan. 2005, 2(1):3-28.
Meade et al., "Enhancing the Cellular Uptake of siRNA Duplexes Following Noncovalent Packaging with Protein Transduction Domain Peptides," Advanced Drug Delivery Reviews, 60, pp. 530-536, 2008.
Miller et al., "Allele-specific Silencing of Dominant Disease Genes," Proceedings of the National Academy of Sciences of USA, Jun. 10, 2003, 100(12):7195-7200.
Mirshahi et al., "The Mineralocorticoid Hormone Receptor and Action in the Eye," Biochem Biophys Res Commun, vol. 219, pp. 150-156, 1996.
Muratovska et al., "Conjugate for Efficient Delivery of Short Interfering RNA (siRNA) into Mammalian Cells," FEBS Letters, 558, pp. 63-68, 2004.
Nakamura et al., "RNA Interference Targeting Transforming Growth Factor-β type II Receptor Suppresses Ocular Inflammation and Fibrosis," Molecular Vision, 10, pp. 703-711, 2004.
Nie Y., et al., "The potential therapeutic of siRNA eye drops in ocular diseases," *Bioscience Hypotheses*, 2, 223-25, 2009.

Okabe et al., "Effect of Benzalkonium Chloride on Transscleral Drug Delivery," Investigative Ophthalmology & Visual Science, vol. 46, No. 2, pp. 703-708 , Feb. 2005.
Olsen et al., "Human Scleral Permeability: Effects of Age, Cryotherapy, Transscleral Diode Laser, and Surgical Thinning," Investigative Ophthalmology & Visual Science, vol. 36, No. 9. pp. 1893-1903, Aug. 1995.
Osborne et al., "Some Current Ideas on the Pathogenesis and the Role of Neuroprotection in Glaucomatous Optic Neuropathy," Eur J Ophthalmol., Apr. 2003, 13Suppl. 3:519-26.
Paddison et al., "Short hairpin RNAs (shRNAs) Induce Sequence-Specific Silencing in Mammalian Cells," Genes Dev, 2002, 16(8):948-958.
Papers filed on Mar. 2, 2012, from opponents in Opposition by Alcon Research, Ltd. against Australian Patent Application No. 2005276245 in the name of Sylentis SAU.
Peral et al., "Effect of Several siRNA in the Treatment of Ocular Hypertension and Glaucoma," Invest. Ophthalmol. Vis. Sci., 48, E-Abstract 4808, 2007.
Pintor et al., "Adenosine Tetraphosphate, $Ap_4$, a Physiological Regulator of Intraocular Pressure in Normotensive Rabbit Eyes," The Journal of Pharmacology and Experimental Therapeutics, vol. 308, No. 2, pp. 468-473, 2004.
Pintor et al., "SiRNA in the Treatment of Ocular Hypertension Targeting Alpha and Beta Adrenoceptors," Invest. Ophthalmol. Vis. Sci., 47, E-Abstract 403, 2006.
Rao et al., "Modulation of Aqueous Humor Outflow Facility by the Rho Kinase-Specific Inhibitor Y-27632," Investigative Opthalmology & Visual Science, Apr. 2001, 42(5): 1029-1037.
Reich et al., "Small Interfering RNA (siRNA) Targeting VEGF effectively Inhibits Ocular Neovascularization in a Mouse Model," Molecular Vision, 2003, 9:210-216.
Ruz et al., "Phase I Study With a New siRNA: SYL040012. Tolerance and Effect on Intraocular Pressure," Investigative Ophthalmology Visual Science, 52, E-Abstract 223, 2011.
Sakaguchi et al., "Chymase and Angiotensin Converting Enzyme Activities in a Hamster Model of Glaucoma Filtering Surgery," Curr Eye Res., May 2002, 24(5):325-331.
Scherer et al., "Approaches for the Sequence-Specific Knockdown of mRNA," Nat. Biotechnology, 2003, 21(12):1457-1465.
Shah et al., "Oculohypotensive Effect of Angiotensin-Converting Enzyme Inhibitors in Acute and Chronic Models of Glaucoma," J Cardiovasc Pharmacol. Aug. 2000, 36(2):169-175.
Stamer et al., "Isolation and Culture of Human Trabecular Meshwork Cells by Extracellular Matrix Digestion," Current Eye Research, pp. 611-617, Jan. 10, 1995.
Studies conducted in the Biochemistry Department of the School of Optics at the Universidad Complutense de Madrid, as filed in the Information Disclosure Statement of Oct. 30, 2008 (in U.S. Appl. No. 11/574,169).
Supuran et al., "Carbonic Anhydrase Inhibitors," Medicinal Research Reviews, 23(2):146-189, 2003.
Tan et al., "Recent Developments in Understanding the Pathophysiology of Elevated Intraocular Pressure," Current Opinion in Opthalmology, vol. 17, pp. 168-174, 2006.
Tolentino et al., "Intravitreal Injection of Vascular Endothelial Growth Factor Small Interfering RNA Inhibits Growth and Leakage in a Nonhuman Primate, Laser-Induced Model of Chorodial Neovascularization," Retina, The Journal of Retinal and Vitreous Diseases, vol. 24, No. 1, 2004, pp. 132-138.
Tuschl et al., "Targeted mRNA degradation by double-stranded RNA in vitro," Genes Dev., 1999, 13(24):3191-3197.
Uprichard et al., The Therapeutic Potential of RNA Interference, FEBS Letters, Oct. 31, 2005 579(26):5996-6007.
Valls et al., "Validation of a Device for Transcorneal Drug Permeation Measure," Journal of Pharmaceutical and Biomedical Analysis, 48, pp. 657-663, 2008.
Vittal et al., "Changes in Gene Expression by Trabecular Meshword Cells in Response to Mechanical Stretching," Investigative Opthalmology & Visual Science, Aug. 2005, 46(8):2857-2868.
Wang et al., Effect of C5-088, an Angiotensin AT1 Receptor Antagonist, on Intraocular Pressure in Glaucomatous Monkey Eyes, Exp Eye Res., May 2005 80(5):629-632. Epub Jan. 4, 2005.

(56) References Cited

OTHER PUBLICATIONS

Wax et al., "Vacuolar H$^+$-ATPase in Ocular Ciliary Epithelium," Proc. Natl. Acad. Sci., vol. 94, pp. 6752-6757, Jun. 1997.
Wetering et al., "Specific Inhibition of Gene Expression Using a Stably Integrated, Inducible Small-Interfering-RNA Vector," EMBO Reports, Jun. 2003, 4(6):609-615.
Wianny et al., "Specific Interference with Gene Function by Double-Stranded RNA in Early Mouse Development," Nat Cell Biol, 2000, 2(2):70-75.
Williams BR, "Role of the Double-Stranded RNA-activated Protein kinase (PKR) in Cell Regulation," Biochem Soc Trans, 1997, 25(2):509-513.
Wirtz et al., "The Genetic Loci of Open-Angle Glaucoma," Ophthalmol. Clin. North Am. 2003 16:505-514.
Wiznerowicz et al., "Conditional Suppression of Cellular Genes: Lentivirus Vector-Mediated Drug-Inducible RNA Interference," Journal of Virology, Aug. 2003, 77(16):8957-8961.
Woodward et al., "The Inflow and Outflow of Anti-Glaucoma Drugs," Trends in Pharmacological Sciences, May 2004, 25(5):238-241.
Xie et al., "Harnessing in vivo siRNA Delivery for Drug Discovery and Therapeutic Development," Drug Discovery Today, Jan. 2006, 11(1-2):67-73.
Yang-Feng et al., "Chromosomal Organization of Adrenergic Receptor Genes," PNAS, 1990, 87:1516-1520.
Yang et al., "Early Growth Response Gene 1 Modulates Androgen Receptor Signaling in Prostate Carcinoma Cells," The Journal of Biological Chemistry, 278(41), pp. 39906-39911, 2003.
Yan et al., "Requirement of NeuroD for Photoreceptor Formation in the Chick Retina," Invest Ophthalmol Vis. Sci., 45(1), pp. 48-58, Jan. 2004.
Office Action dated Jul. 14, 2008 in corresponding U.S. Appl. No. 11/360,305.
Office Action dated Jan. 29, 2009 in corresponding U.S. Appl. No. 11/360,305.
Office Action dated Nov. 12, 2008 in corresponding U.S. Appl. No. 11/574,169.
Final Office Action dated May 8, 2009 in corresponding U.S. Appl. No. 11/574,169.
Office Action dated Nov. 3, 2009 in corresponding U.S. Appl. No. 12/170,078.
Office Action dated Oct. 15, 2009 in corresponding U.S. Appl. No. 12/170,104.
Office Action dated Oct. 15, 2009 in corresponding U.S. Appl. No. 12/170,157.
Office Action dated Oct. 30, 2009 in corresponding U.S. Appl. No. 12/170,116.
Office Action dated Oct. 30, 2009 in corresponding U.S. Appl. No. 12/170,132.
Office Action dated Oct. 19, 2009 in corresponding U.S. Appl. No. 12/170,148.
Office Action dated Dec. 4, 2009 in corresponding U.S. Appl. No. 11/574,169.
Office Action dated Mar. 19, 2010 in corresponding U.S. Appl. No. 12/170,078.
Office Action dated Mar. 22, 2010 in corresponding U.S. Appl. No. 12/170,104.
Office Action dated Mar. 19, 2010 in corresponding U.S. Appl. No. 12/170,116.
Office Action dated Mar. 22, 2010 in corresponding U.S. Appl. No. 12/170,132.
Office Action dated Mar. 22, 2010 in corresponding U.S. Appl. No. 12/170,148.
Office Action dated Mar. 22, 2010 in corresponding U.S. Appl. No. 12/170,157.
Office Action dated Mar. 25, 2010 in corresponding U.S. Appl. No. 12/563,530.
Final Office Action dated Jul. 22, 2010 in corresponding U.S. Appl. No. 11/574,169.
Office Action dated Sep. 7, 2010 in corresponding U.S. Appl. No. 11/574,169.
Office Action dated Sep. 23, 2010 in corresponding U.S. Appl. No. 12/170,078.
Office Action dated Sep. 23, 2010 in corresponding U.S. Appl. No. 12/170,104.
Office Action dated Sep. 23, 2010 in corresponding U.S. Appl. No. 12/170,116.
Office Action dated Sep. 23, 2010 in corresponding U.S. Appl. No. 12/170,132.
Jimenez et al., Response to Nonfinal Office Action dated Jul. 14, 2007, filed electronically on Nov. 14, 2008 for U.S. Appl. No. 11/360,305, 40 pages.
Office Action dated Sep. 23, 2010 in corresponding U.S. Appl. No. 12/170,148.
Office Action dated Sep. 23, 2010 in corresponding U.S. Appl. No. 12/170,157.
Office Action dated Aug. 10, 2011 in corresponding U.S. Appl. No. 12/091,498.
Office Action dated Mar. 19, 2012 in corresponding U.S. Appl. No. 12/170,104.
Office Action dated Mar. 19, 2012 in corresponding U.S. Appl. No. 12/170,116.
Office Action dated Mar. 19, 2012 in corresponding U.S. Appl. No. 12/170,132.
Office Action dated Mar. 19, 2012 in corresponding U.S. Appl. No. 12/170,148.
Office Action dated Mar. 19, 2012 in corresponding U.S. Appl. No. 12/170,157.
Bian et al., "High-Dose siRNAs Upregulate Mouse Eri-1 at both Transcription and Posttranscription Levels," PLoS One, 6(10), pp. 1-15, 2011.
Coelho et al., "Safety and Efficacy of RNAi Therapy for Transthyretin Amyloidosis," N. Engl. J. Med. 369(9), pp. 819-829, 2013.
Gonzalez et al., "Phase 2 of Bamosiran (SYL040012), a Novel RNAi Based Compound for the Treatment of Increased Intraocular Pressure Associated to Glaucoma," Investigative Ophthalmology & Visual Science, vol. 55, 564, Apr. 2014, including ARVO Annual Meeting Abstract poster.
Moreno-Montanes et al., "Phase I Clinical Trial of SYL040012,a Small Interfering RNA Targeting β-Adrenergic Receptor 2, for Lowering Intraocular Pressure," Molecular Therapy, vol. 22, No. 1, pp. 226-232, 2014.
Pecot et al., "RNA interference in the clinic: challenges and future directions," Nature Reviews, 11, pp. 59-67, 2011.
González et al., "Bamosiran ophthalmic solution for the treatment of glaucoma: Results of the Phase IIB SYLTAG study," 2016 Annual Meeting in Seattle, Wash. May 1-5, 2016 (poster presented on May 3, 2016).
Martinez et al., In Vitro and in Vivo Efficacy of SYL040012, a Novel siRNA Compound for Treatment of Glaucoma, Molecular Therapy, vol. 22, No. 1, pp. 81-91, 2014.
Moreno-Montanes et al., "Phase I Clinical Trial of SYL040012, a Small Interfering RNA Targeting Beta-Adrenergic Receptor 2, for Lowering Intraocular Pressure," Molecular Therapy, vol. 22, pp. 226-232, 2014.
Jimenez Anton et al., Office Action dated Aug. 3, 2016 in corresponding U.S. Appl. No. 14/425,466, 15 pages.
Jimenez Anton et al., Office Action dated Nov. 12, 2015 in corresponding U.S. Appl. No. 14/425,466, 13 pages.
EU Clinical Trials Register, EudraCT No. 2011-001849-33, Estonia, EEA CTA, Mar. 8, 2012, 7 pages.
EU Clinical Trials Register, EudraCT No. 2011-001849-33, Spain, EEA CTA, Mar. 20, 2012, 8 pages.
EU Clinical Trials Register, EudraCT No. 2011-001849-33, Germany, EEA CTA, May 21, 2012, 7 pages.

\* cited by examiner

SEQ ID NO: 1

Human ADRB2 mRNA target sequence: CAUUGUGCAUGUGAUCCAG

SEQ ID NO: 2

| SYL040012: Sense | 5' - <u>CAUUGUGCAUGUGAUCCAG</u> dT dT - 3' |
|---|---|
| Antisense | 3'- dT dT <u>GUAACACGUACACUAGGUC</u> - 5' |

SEQ ID NO: 3

| Sense | 5' - <u>CAUUGUGCAUGUGAUCCAG</u>- 3' |
|---|---|
| Antisense | 3'- <u>GUAACACGUACACUAGGUC</u> - 5' |

SEQ ID NO: 4

| Sense | 5' - <u>CAUUGUGCAUGUGAUCCAG</u> - 3' |
|---|---|
| Antisense | 3'- dT dT <u>GUAACACGUACACUAGGUC</u> - 5' |

SEQ ID NO: 5

| Sense | 5' - <u>CAUUGUGCAUGUGAUCCAG</u> dT dT - 3' |
|---|---|
| Antisense | 3'- <u>GUAACACGUACACUAGGUC</u> - 5' |

SEQ ID NO: 6

| Sense | 5' - <u>CAUUGUGCAUGUGAUCCAG</u> dU dU - 3' |
|---|---|
| Antisense | 3'- dU dU <u>GUAACACGUACACUAGGUC</u> - 5' |

Underline represents hybridization region

Figure 7

SIRNA AND THEIR USE IN METHODS AND COMPOSITIONS FOR THE TREATMENT AND/OR PREVENTION OF EYE CONDITIONS

BACKGROUND OF THE INVENTION

Glaucoma is defined as the process of ocular tissue destruction caused by a sustained elevation of intra ocular pressure (IOP) above its normal physiological limits[1]. In open angle glaucoma (OAG), elevated IOP causes a progressive optic neuropathy due to loss of retinal ganglion cells that ultimately leads to blindness[2]. In angle-closure glaucoma the sudden high rise in IOP often renders the eye blind. Glaucoma is the second leading cause of blindness worldwide[3] and the prevalence is increasing worldwide[4]. Blindness in glaucoma is caused by a degenerative process of the retina and optic nerve, but is functionally associated with impairments in the balance between aqueous humor (AH) secretion and outflow. AH is secreted by cells of the ciliary body (CB) and outflow can occur through one of two pathways: the trabecular meshwork pathway and the uveoscleral pathway[5].

Current treatment for glaucoma is not able to restore vision-loss caused by glaucoma, but is focused on IOP reduction[6]. Controlling IOP has been shown to protect against damage to the optic nerve in glaucoma[5,7]. There are five drug classes currently used to achieve IOP reduction: α-adrenergic agonists, β-adrenergic antagonists, cholinergic agonists, prostaglandins and carbon anhydrase inhibitors. If no efficacy in reducing IOP is achieved with any of these drugs, laser therapy can be applied to the trabecular meshwork in order to increase AH outflow. The last therapeutic resource is a surgical procedure to create a new route for AH outflow[8].

Current treatments for increased IOP associated with glaucoma have relatively few ocular side effects but may have systemic side effects if the compound reaches the bloodstream[9,10,11]. Treatments that are systemically better tolerated, such as prostaglandins, have many local tolerance issues[12]. This fact together with the required frequency of instillations in order to maintain adequate levels of IOP makes treatment compliance a challenge for patients[13]. Failure to comply with therapy cannot only allow for disease progression but can also have a reboot effect causing sudden increases in IOP that can be very damaging to the optic nerve.

Prostaglandins and beta-blockers are the preferred IOP-lowering agents.[12,14] Prostaglandins lower IOP extremely well and are safe systemically but have several associated ocular side effects,[15] i.e., darkening of the iris color, lash growth, periocular pigmentation, and hyperemia. Less frequent ocular side effects of this drug class are intraocular inflammation, cystoid macular edema, and reactivation of ocular corneal herpes viral infections[16]. Prostaglandin analogs are contraindicated during pregnancy because of the potential risk of premature labor.

Topical application of beta blockers reduces IOP by decreasing AH production and not by increasing its outflow. Topically administered beta-blockers are absorbed via the conjunctival epithelium, lacrimal channel, nasal mucosa and gastrointestinal tract into the systemic circulation inducing systemic adverse reactions[17-19]. In the eye, adrenergic receptors have been located at blood vessels that irrigate the ciliary body and trabecular meshwork, where their main effect is vasoconstriction, although their involvement in aqueous humour secretion has also been described. Previous studies in rabbits' eyes showed high density of β-adrenergic receptors in conjunctival, corneal and ciliary process epithelium. β-adrenergic receptors were also present in corneal endothelium, lens epithelium, choroid and extraocular muscle. Most of the β-adrenergic receptors detected in eye belong to the β2-type[20-23].

RNA interference (RNAi) is a technology based on the principle that small, specifically designed, chemically synthesized double-stranded RNA fragments can mediate specific messenger RNA (mRNA) degradation in the cytoplasm and hence selectively inhibit the synthesis of specific proteins. This technology has emerged as a very powerful tool to develop new compounds aimed at blocking and/or reducing anomalous activities in defined proteins[24,25]. Compounds based on RNA interference can be rationally designed to block expression of any target gene, including genes for which traditional small molecule inhibitors cannot be found.[26] Examples of successful use of RNAi in therapeutics include inhibition of HIV-1 replication in human cells[27] and knock-down of tau and apolipoprotein precursor protein in animal models of Alzheimer's disease.[28] Even though RNAi was discovered just over a decade ago, a few of these compounds are already in advanced phases of clinical trials, i.e., RTP801 (Quark Pharmaceuticals, Fremont, Pa., phase II) for treating age-related macular degeneration and ALN-RSV01 (Alnylam Pharmaceuticals, Cambridge, Mass., phase II) for treating respiratory syncytial virus[29,30]. RNA interference is a very attractive approach to chronic conditions, since upon cessation of treatment the silenced protein has to be re-synthesized in order to recover its biological activity. Hence the effects of compounds based on RNA interference are in general more prolonged than those of conventional treatments[24,31].

The eye is a relatively isolated tissue compartment; this particularity provides several advantages to the use of siRNA based therapies. Local delivery of compounds to the eye limits systemic exposure and reduces the amount of compound needed. This allows for local silencing of a gene and reducing the likelihood of wide spread silencing outside the eye. In addition, the immune system has a limited access to the eye; therefore immune responses to the compound are less likely to occur[32].

Continuing the work described in WO2006/021817, we have developed an siRNA: SYL040012, as identified in SEQ ID NO: 2, a chemically synthesized, unmodified, 19 bp double-stranded oligonucleotide with dinucleotide overhangs at 3' of deoxythymidine, able to selectively inhibit synthesis of β2-adrenergic receptor, indicated for the treatment of elevated IOP in patients with ocular hypertension, open angle glaucoma, and other related diseases.

The compound has proven efficacy inhibiting expression of its target in cell cultures and in lowering IOP in normotensive rabbits and in a model of increased IOP in rabbits.

BxPC3 and MDA-MB-231 in cells treated with either 100 nM SYL040012, scramble sequence or vehicle. * indicates statistically significance level of p<0.5 with respect to time-point 0.

Figure 2:
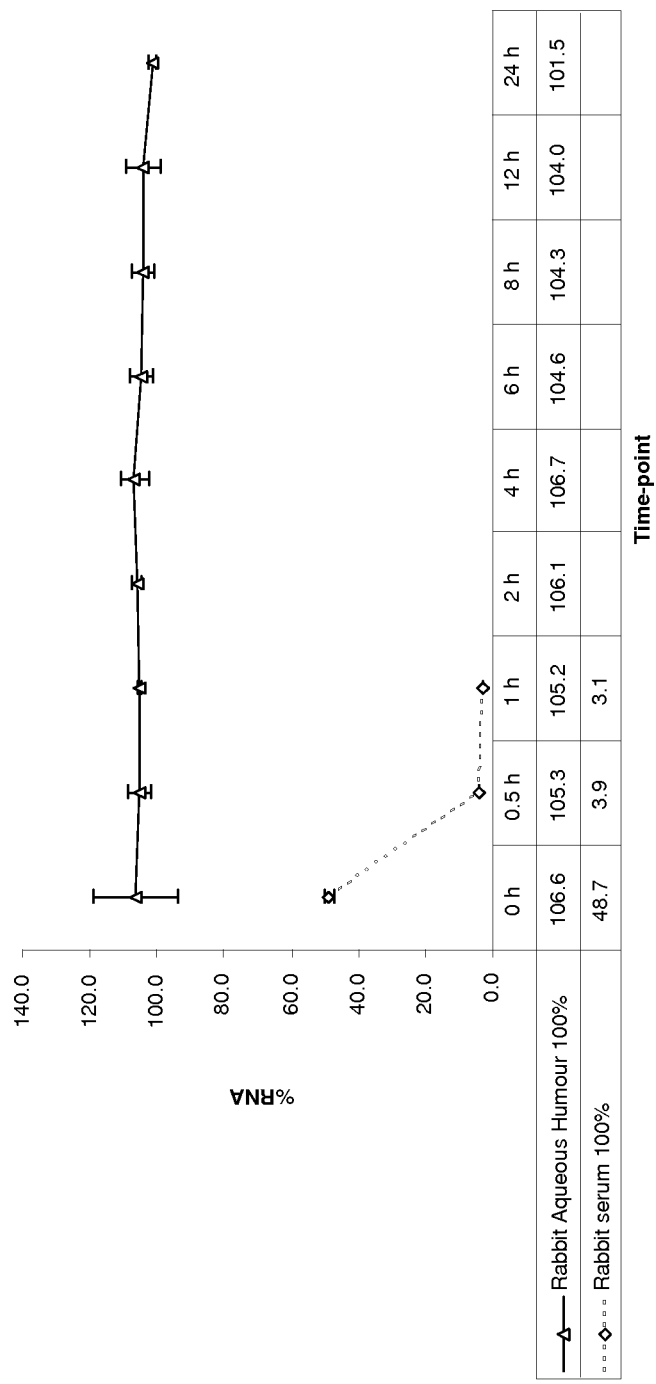

FIG. 2: Stability of SYL040012 in biological fluids. Stability of SYL040012 was assessed in rabbit aqueous humor and rabbit serum by native-HPLC at different time-points by spiking freshly obtained samples of both biological fluids with a 20 μM solution of SYL040012 in PBS at time 0. Results are represented as percentage of the initial amount. Data represent means±S.D. of 2 independent analyses.

Figures 3A, 3B, 3C, 3D, 3E, 3F:
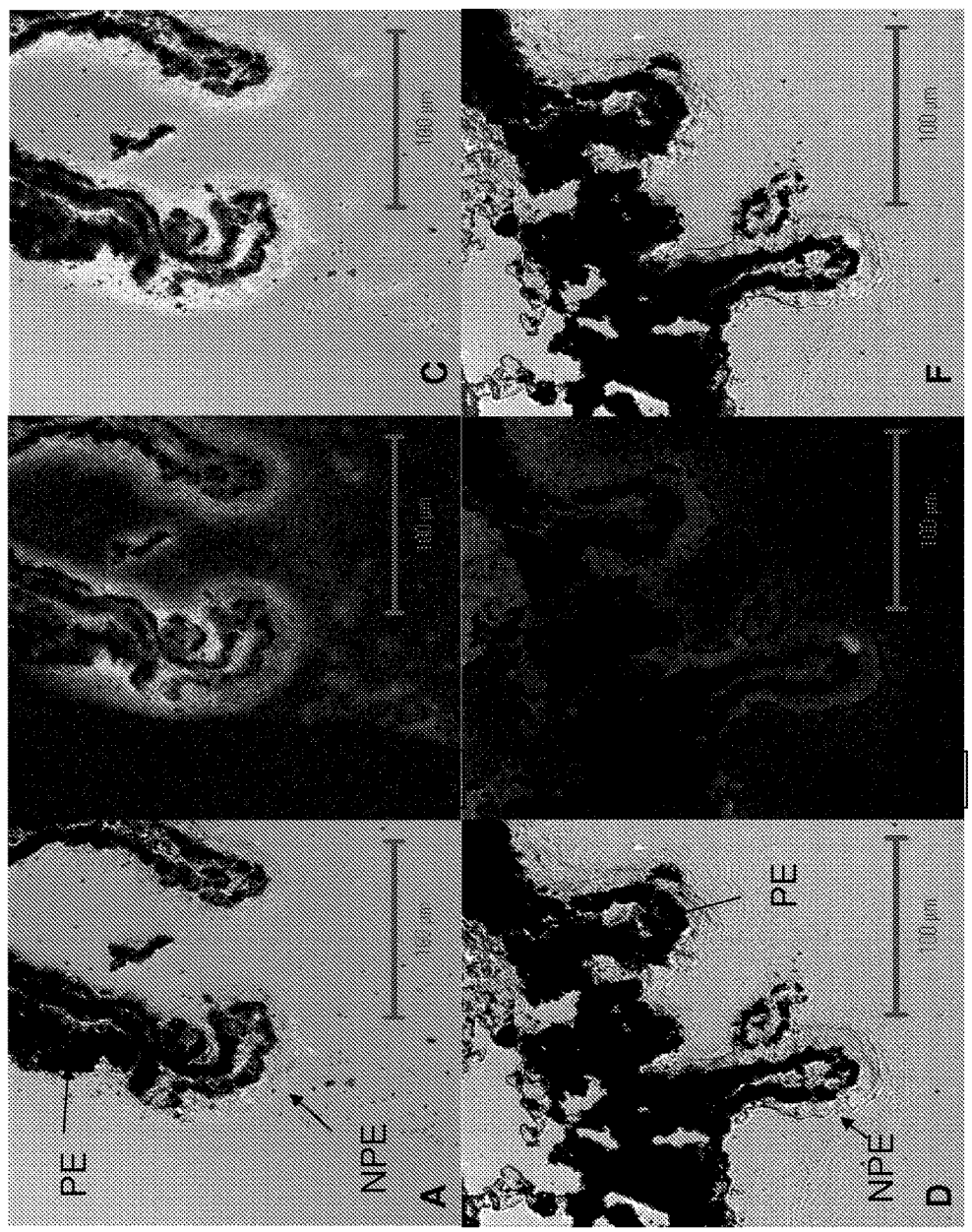

FIG. 3: Reduction of eGFP levels in the ciliary body following treatment with an eGFP-siRNA. eGFP transgenic mice we treated with three doses of 160 μg/day. 48 h after the last administration animals were sacrificed, the eyes enucleated and processed for fluorescence microscopy. Left panels show Nomarski microphotographs of the ciliary body of a PBS treated animal (A) and of an eGFP-siRNA treated animal (B). Middle panels show fluorescence microphotographs of a PBS treated animal (C) and of an eGFP-siRNA treated animal (D). The right panel show merges of Nomarski and fluorescence microphotographs. NPE: Non-pigmented epithelium; PE: pigmented epithelium.

FIG. 4: In vivo efficacy of SYL040012 in rabbits. (A) IOP lowering effect of SYL040012: two groups of NZW rabbits were treated with either SYL040012 (20 nmol/day) or PBS over a period of 4 consecutive days. IOP was assessed every two hours up to 8 h after each administration, the same schedule was followed on days 5-10 but no compounds were given. (B) Specificity of the effect of SYL040012: two groups of NZW rabbits were treated with either 100 nM of a scramble siRNA or with PBS. IOP was assessed as described above. (C) Long-term IOP lowering effect of SYL040012: two groups of rabbits were administered with either 20 nmol/day SYL040012 or PBS over two periods of four days separated from each other by a drug-free period of 3 days. IOP was assessed as described above from days 1-13. Representative experiments are shown.

FIG. 5: Efficacy of SYL040012 in a rabbit model of high intraocular pressure induced by oral water overloading. (A) Dose response of SYL040012 on IOP: animals were administered either SYL040012 at one of the following doses: 10, 20, 40, or 60 nmol/eye/day or PBS over a period of four days. 120 min after the last dose ocular hypertension was induced by oral water overloading. IOP was assessed coinciding with the last dosing, 60 min and immediately prior to oral water overloading and a total of 10 times with a 25 minute-interval between measurements after oral water overloading. Data represent means±s.e.m. of 2 animals per group. (B) Specificity of SYL040012 on IOP: animals were administered either 40 nmol/eye/day of SYL040012, a scramble siRNA or PBS as mentioned above. Oral water overloading and IOP measurements were performed as mentioned in A. Data represent means±s.e.m. of 12 animals for SYL040012; 11 animals for PBS and 2 animals for scramble siRNA. (C) Reduction of ADRB2 levels in animals treated with SYL040012. Animals were treated as stated in B and immediately after the last IOP measurement they were sacrificed, eyes were enucleated and cornea, lacrimal gland and ciliary body were isolated. Total RNA was extracted and expression of ADRB2 was analyzed by real time PCR. Data represent means±s.e.m. of 3 animals per group. Statistical significance was calculated by comparing each treated eye structure with its PBS treated counterpart using unpaired Student t tests and was as follows: ***p<0.001.

FIG. 6: IOP curves in response to doses A and B of SYL040012. A. IOP evolution in 12 healthy subjects in response to repeated administration of dose A of SYL040012; B. IOP evolution in the subgroup of subjects that showed a decrease in IOP greater than 20% in response to dose A of SYL040012 (n=5). C: IOP evolution in 12 healthy subjects in response to repeated administrations of dose B of SYL040012. Data represent mean±standard error of the mean (s.e.m) of 12 subjects in A and C and 5 subjects in B. Statistical significance was calculated by Repeated Measures two-way ANOVA and Bonferroni's corrections were made for the subsequent pairwise comparisons and was as follows: *p<0.001; p<0.01 and *p<0.05.

FIG. 7: siNA molecules of the invention. This figure shows oligonucleotides sequences for siNA molecules encompassed in the present invention.

SUMMARY OF THE INVENTION

The present invention relates to methods, compositions and dosages that decrease IOP of the eye, comprising SYL040012, a 19 nucleotide double-stranded RNA molecule with dinucleotide deoxythymidine overhangs at 3'. The compositions of the present invention comprise SYL040012 in a saline solution such as PBS and pharmaceutically acceptable excipients, thus allowing their instillation on the eye, i.e. as eyedrops. The dosages of the invention comprise a daily instillation of an eyedrop of between about 30 μl and about 40 μl comprising between about 0.6 mg and 0.9 mg of SYL040012.

The present invention relates to methods, compositions and dosages that decrease IOP of the eye. The compositions of the invention comprise short interfering nucleic acid molecules (siNA) that decrease expression of adrenergic receptor beta 2 (ADRB2) gene, which, as indicated previously, decreases production of aqueous humour within the anterior chamber of the eye. The compositions of the invention can be used in the preparation of a medicament for the treatment of an eye condition displaying increased IOP such as glaucoma, infection, inflammation, uveitis, and diabetic retinopathy. The methods of the invention comprise the administration to a patient in need thereof of an effective amount of one or more siNAs of the invention in an effective dosing regime.

The compositions of the invention comprise short interfering nucleic acid molecules (siNA) that decrease or inhibit expression of adrenergic receptor beta 2 (ADRB2), a gen associated with production of intraocular fluid, i.e. aqueous humor. The present invention encompasses compositions and methods of use of short interfering nucleic acid (siNA) including, but not limited to, short interfering RNA (siRNA), double-stranded RNA (dsRNA), and short hairpin RNA (shRNA) molecules capable of mediating RNA interference (RNAi) against the target gene, ADRB2. In preferred embodiments, the siNA used in the methods of the invention are dsRNA. siNAs of the invention can be unmodified or chemically modified.

The methods of the invention comprise the administration to a patient in need thereof of an effective amount of an siNA of the invention. In preferred embodiments the methods of the invention provide a sustained decrease in IOP when compared with the duration of IOP decrease that results from administration of commercially available drugs such as Xalatan, Trusopt and Timoftol.

Methods of the invention also encompass administration of one or more siNAs of the invention in combination with one or more other therapeutics that decrease IOP including, but not limited to, commercially available drugs.

Methods of the invention also encompass administration of the composition of the invention via instillation on the ocular surface. When the siRNA is administered directly to the eye, generally an amount of between about 0.01 mg and about 100 mg per eye per day, between about 0.04 mg and about 80 mg per eye per day, between about 0.04 mg and about 20 mg per eye per day, between about 0.08 mg and about 10 mg per eye per day, between about 0.08 mg and about 1.2 mg per eye per day, between about 0.3 and about 0.9 mg per eye per day, or between about 0.08 mg and about 0.9 mg per eye per day, per day of siNA is administered.

DETAILED DESCRIPTION OF THE INVENTION

The present invention relates to methods, compositions and dosages that decrease IOP of the eye. The compositions of the invention comprise short interfering nucleic acid molecules (siNA) that decrease expression of adrenergic receptor beta 2 (ADRB2) gene, which, as indicated previously, the expression product of which decreases production of aqueous humour within the anterior chamber of the eye. The compositions of the invention can be used in the preparation of a medicament for the treatment of an eye condition displaying increased IOP such as glaucoma. The methods of the invention comprise the administration to a patient in need thereof of an effective amount of one or more siNAs of the invention in an effective dosing regime.

Design of siNAs siNAs of the invention are designed to modulate the activity by decreasing or inhibiting the expression of ADRB2, thus affecting IOP. In one embodiment, a decrease in or inhibition of the target gene expression decreases the production of intraocular fluid e.g. aqueous humour. GenBank accession number for ADRB2, the present target gene, is NM_000024.

As used herein "siNAs" of the invention refers to a double stranded oligonucleotide capable of mediating target mRNA cleavage via RNA interference. It is preferred to the term siRNA to avoid confusion, given that it is a common practice in the field to include modified non-canonical bases within the molecule structure, and on occasion a deoxyribonucleotide, including single-stranded thymidine overhangs at the ends of the double-stranded portion.

A gene is "targeted" by a siNA according to the invention when, for example, the siNA molecule selectively decreases or inhibits the expression of the gene. The phrase "selectively decrease or inhibit" as used herein encompasses siNAs that decrease expression of one gene as well those that decrease the expression of more than one gene. In cases where an siNA decreases expression of more than one gene, the gene that is targeted is decreased at least about two times, about three times, about four times, about five times, about ten times, about twenty five times, about fifty times, or about one hundred times as much as any other gene. Alternatively, a siNA targets a gene when the siNA hybridizes under stringent conditions to the gene transcript. siNAs can be tested either in vitro or in vivo for the ability to target a gene.

A short fragment of the target gene's mRNA sequence (e.g. 19-40 nucleotides in length) is chosen for the sequence of the siNA of the invention. In one embodiment the siNA is a siRNA. In preferred embodiments, the criteria for choosing a sequence fragment from the target gene mRNA to be a candidate siRNA molecule include 1) a sequence from the target gene mRNA that is at least 50-100 nucleotides from the 5' or 3' end of the native mRNA molecule, 2) a sequence from the target gene mRNA that has a G/C content of between 30% and 70%, most preferably around 50%, 3) a sequence from the target gene mRNA that does not contain repetitive sequences (e.g. AAA, CCC, GGG, UUU, AAAA, CCCC, GGGG, UUUU), 4) a sequence from the target gene mRNA that is accessible in the mRNA, and 5) a sequence from the target gene mRNA that is unique to the target gene. The sequence fragment from the target gene mRNA may meet one or more criteria identified above. In embodiments where a fragment of the target gene mRNA meets less than all of the criteria identified supra, the native sequence may be altered such that the siRNA conforms with more of the criteria than does the fragment of the target gene mRNA. In preferred embodiments, the siRNA has a G/C content below 60% and/or lacks repetitive sequences.

In one specific embodiment, the portion of the siNA that is complementary to the target region is perfectly complementary to the target region. In another specific embodiment, the portion of the siNA that is complementary to the target region is not perfectly complementary to the target region. siNA with insertions, deletions, and point mutations relative to the target sequence are also encompassed by the invention. Thus, sequence identity may be calculated by sequence comparison and alignment algorithms known in the art (see Gribskov and Devereux, Sequence Analysis Primer, Stockton Press 1991, and references cited therein) and calculating the percent difference between the nucleotide sequences by, for example, the Smith-Waterman algorithm as implemented in the BESTFIT software program using default parameters (e.g. University of Wisconsin Genetic Computing Group). Greater than 90%, 95%, or 99% sequence identity between the siNA and the portion of the target gene is preferred. Alternatively, the complementarity between the siNA and native RNA molecule may be defined functionally by hybridization. A siNA sequence of the invention is capable of hybridizing with a portion of the target gene transcript under stringent conditions (e.g. 400 mM NaCl, 40 mM PIPES pH 6.4, 1 mM EDTA, 50° C. or 70° C. hybridization for 12-16 hours; followed by washing). A siNA sequence of the invention can also be defined functionally by its ability to decrease or inhibit the expression of a target gene. The ability of a siNA to affect gene expression can be determined empirically either in vivo or in vitro.

In addition to siNAs which specifically target only one gene, degenerate siNA sequences may be used to target homologous regions of multiple genes. WO2005/045037 describes the design of siNA molecules to target such homologous sequences, for example by incorporating non-canonical base pairs, for example mismatches and/or wobble base pairs, that can provide additional target sequences. In instances where mismatches are identified, non-canonical base pairs (for example, mismatches and/or wobble bases) can be used to generate siNA molecules that target more than one gene sequence. In a non-limiting example, noncanonical base pairs such as UU and CC base pairs are used to generate siNA molecules that are capable of targeting sequences for differing targets that share sequence homology. As such, one advantage of using siNAs of the invention is that a single siNA can be designed to include a nucleic acid sequence that is complementary to the nucleotide sequence that is conserved between homologous genes. In this approach, a single siNA can be used to inhibit expression of more than one gene instead of using more than one siNA molecule to target different genes.

Preferred siNA molecules of the invention are double-stranded. In one embodiment, double stranded siNA molecules comprise blunt-ends. In another embodiment, double stranded siNA molecules comprise overhanging nucleotides (e.g. 1-5 nucleotide overhangs, preferably 2 nucleotide overhangs). In a specific embodiment, the overhanging nucleotides are 3' overhangs. In another specific embodiment, the overhanging nucleotides are 5' overhangs. Any type of nucleotide can be a part of the overhang. In one embodiment, the overhanging nucleotide or nucleotides are ribonucleic acids. In another embodiment, the overhanging nucleotide or nucleotides are deoxyribonucleic acids. In a preferred embodiment, the overhanging nucleotide or nucleotides are thymidine nucleotides. In another embodiment, the overhanging nucleotide or nucleotides are modified or non-classical nucleotides. The overhanging nucleotide or nucleotides may have non-classical internucleotide bonds (e.g. other than phosphodiester bond).

In preferred embodiments, siNA compositions of the invention are designed to target SEQ ID NO: 1. Further embodiments refer to siNAs identified by SEQ ID NO 1, 2, 3, 4, 5 and 6. In another embodiment, the preferred siNA of the invention is SEQ ID NO: 2 (SYL040012). This preferred siNA SYL040012, is a 19 nt long unmodified double stranded RNA molecule with dinucleotide overhangs at the 3' ends comprising deoxythymidine bases, as depicted in FIG. 7.

Synthesis of siNAs siNAs designed by methods described above can be synthesized by any method known in the art. RNAs are preferably chemically synthesized using appropriately protected ribonucleoside phosphoramidites and a conventional DNA/RNA synthesizer. Additionally, siRNAs can be obtained from commercial RNA oligo synthesis suppliers, including, but not limited to, Proligo (Hamburg, Germany), Dharmacon Research (Lafayette, Colo., USA), Glen Research (Sterling, Va., USA), ChemGenes (Ashland, Mass., USA), and Cruachem (Glasgow, UK), Qiagen (Germany), Ambion (USA) and Invitrogen (Scotland). Alternatively, siNA molecules of the invention can be expressed in cells by transfecting the cells with vectors containing the reverse complement siNA sequence under the control of a promoter. Once expressed, the siNA can be isolated from the cell using techniques well known in the art.

In embodiments where the siRNA is a double-stranded RNA (dsRNA), an annealing step is necessary if single-stranded RNA molecules are obtained. Briefly, combine 30 ml of each RNA oligo 50 mM solution in 100 mM potassium acetate, 30 mM HEPES-KOH pH 7.4, 2 mM magnesium acetate. The solution is then incubated for 1 minute at 90° C., centrifuged for 15 seconds, and incubated for 1 hour at 37° C.

In embodiments where the siRNA is a short hairpin RNA (shRNA); the two strands of the siRNA molecule may be connected by a linker region (e.g., a nucleotide linker or a non-nucleotide linker).

5.3 Chemical Modification of siNAs

The siNAs of the invention may contain one or more modified nucleotides and/or non-phosphodiester linkages. Chemical modifications well known in the art are capable of increasing stability, availability, and/or cell uptake of the siNA. The skilled person will be aware of other types of chemical modification which may be incorporated into RNA molecules (see International Publications WO031070744 WO2005/045037 or WO2008/104978 for an overview of types of modifications).

In one embodiment, modifications can be used to provide improved resistance to degradation or improved uptake. Examples of such modifications include phosphorothioate internucleotide linkages, 2'-O-methyl ribonucleotides (especially on the sense strand of a double stranded siRNA), 2'-deoxy-fluoro ribonucleotides, 2'-deoxy ribonucleotides, "universal base" nucleotides, 5-C-methyl nucleotides, and inverted deoxyabasic residue incorporation (see generally GB2406568).

In another embodiment, modifications can be used to enhance the stability of the siRNA or to increase targeting efficiency. Modifications include chemical cross linking between the two complementary strands of an siRNA, chemical modification of a 3' or 5' terminus of a strand of an siRNA, sugar modifications, nucleobase modifications and/or backbone modifications, 2'-fluoro modified ribonucleotides and 2'-deoxy ribonucleotides (see generally International Publication WO2004/029212).

In another embodiment, modifications can be used to increase or decrease affinity for the complementary nucleotides in the target mRNA and/or in the complementary siNA strand (see generally International Publication WO2005/044976). For example, an unmodified pyrimidine nucleotide can be substituted for a 2-thio, 5-alkynyl, 5-methyl, or 5-propynyl pyrimidine. Additionally, an unmodified purine can be substituted with a 7-deza, 7-alkyl, or 7-alkenyl purine.

In another embodiment, when the siNA is a double-stranded siRNA, the 3'-terminal nucleotide overhanging nucleotides are replaced by deoxyribonucleotides, see for example Elbashir et al[33]

Demonstration of Therapeutic Utility

The compositions and methods of the invention are preferably tested in vitro, and then in vivo, for the desired therapeutic activity prior to use in humans. For example, in vitro assays which can be used to determine whether administration of a specific therapeutic protocol is indicated, include in vitro cell culture assays in which a candidate siNA is administered to cells (e.g., rabbit non-pigmented cilliary epithelium cells (NPE), human cilliary epithelium cells (OMDC), or human embryonic kidney cells (HEK293) in vitro and the effect of such protocol upon the cells is observed, e.g., decreased or inhibited expression of the target gene.

Compounds for use in therapy can be tested in suitable animal model systems prior to testing in humans, including but not limited to in rabbits, rats, mice, chicken, cows, monkeys, hamsters, etc. For example, the New Zealand rabbit is the preferred standard in experimental platforms designed to study IOP. It is easy to handle and it has a big eye, similar in size to the human organ. In addition, present equipment to measure IOP is not suited to use in animals with small eyes such as mice or rats. Finally, rabbits have an IOP that can be reduced to 40% of its normal (or pre-drug) value using local commercial hypotensive medication. Thus, although it is possible to generate rabbit glaucoma models (for example, surgically blocking episclerotic veins or artificially occluding the trabecular meshwork), generally those in the field prefer models in which ocular structures remain intact.

Therapeutic Methods

The present invention encompasses methods for treating, preventing, or managing an eye disorder associated with increased IOP in a patient (e.g., a mammal, especially humans) comprising administering an effective amount of one or more siNAs of the invention. In a specific embodiment, the disorder to be treated, prevented, or managed is glaucoma. Any type of glaucoma that is associated with IOP can be treated with the methods of the present invention including, but not limited to, Open Angle Glaucoma (e.g., Primary Open Angle Glaucoma, Pigmentary Glaucoma, and Exfoliative Glaucoma, Low Tension Glaucoma), Angle Closure Glaucoma (also known clinically as closed angle glaucoma, narrow angle glaucoma, pupillary block glaucoma, and ciliary block glaucoma) (e.g., Acute Angle Closure Glaucoma and Chronic Angle Closure Glaucoma), Aniridic Glaucoma, Congenital Glaucoma, Juvenile Glaucoma, Lens-Induced Glaucoma, Neovascular Glaucoma, Post-Traumatic Glaucoma, Steroid-Induced Glaucoma, Sturge-Weber Syndrome Glaucoma, and Uveitis-Induced Glaucoma.

Therapeutic treatments with siRNAs directed against specific target genes are expected to be beneficial over small molecule topical ocular drops by increasing the length of time that effect is observed, thereby allowing less frequent dosing and greater patient compliance.

In preferred embodiments, the siNAs used in the therapeutic methods of the invention decrease or inhibit the expression of genes that effect IOP, such as adrenergic receptor beta 2. In further preferred embodiments of the invention, the siNAs used in the therapeutic methods of the invention are targeted to SEQ ID NO: 1. In a specific preferred embodiment, the siNA is 21 to 30 nucleotides in length and comprises SEQ ID NO: 3. Specifically preferred is SYL040012, with SEQ ID NO: 2 having no modifications, i.e. no non canonical bases, and comprising TT overhangs on both 3' ends.

In preferred embodiments, the methods of the invention provide a sustained decrease in IOP that lasts for longer than 8, 10, 12, or 14 hours, more preferably for several days (e.g., 2 days, 3 days, 4 days, or 5 days), after the last administration of siNA. In such embodiments, the effect (i.e., decreased IOP) of administered siNAs of the invention is longer lasting than the duration of IOP decrease that typically results from administration of presently commercially available drugs (e.g., XALATAN™, TRUSOPT™, and Timoftol). The siNAs of the invention that provide sustained IOP decreasing action can be administered in a regimen such that IOP is continually decreased without daily administration of the siNA. In a specific embodiment, a treatment regimen can include consecutive cycles of administration (e.g., one dose of siNA given daily for four days) and non-administration (e.g., 3 or 4 days with no treatment given) while still eliciting a continual decrease in IOP.

In one embodiment, a single type of siNA is administered in the therapeutic methods of the invention. In another embodiment, an siNA of the invention is administered in combination with another siNA of the invention and/or with one or more other non-siNA therapeutic agents useful in the treatment, prevention or management of an eye disorder associated with increased IOP. The term "in combination with" is not limited to the administration of therapeutic agents at exactly the same time, but rather it is meant that the siNAs of the invention and the other agent are administered to a patient in a sequence and within a time interval such that the benefit of the combination is greater than the benefit if they were administered otherwise. For example, each therapeutic agent may be administered at the same time or sequentially in any order at different points in time; however, if not administered at the same time, they should be administered sufficiently close in time so as to provide the desired therapeutic effect. Each therapeutic agent can be administered separately, in any appropriate form and by any suitable route.

Dosage

As used herein, an "effective amount" refers to that amount of a siNA of the invention sufficient to treat or manage an eye disorder associated with increased IOP and, preferably, the amount sufficient to decrease IOP. For treatment of increased IOP in humans, it is preferred to reduce IOP so that IOP is between about 14 and 20 mm Hg. However, any reduction in IOP as compared to pretreatment IOP is advantageous, whether the compounds of the invention are delivered alone, or in combination with another suitable therapeutic (e.g., the invention contemplates a decrease in IOP greater that about 5%, about 10%, about 25%, about 30%, about 35%, about 40%, about 50%, or about 60% of pretreatment IOP). In some embodiments, the compounds of the invention can cause a decrease in IOP that is between about 1% and about 99%, between about 5% and about 90%, between about 10% and about 80%, between about 20% and about 50%, or between about 25% and about 45% of pretreatment IOP. Preferably, the decrease in IOP is between about 25% and about 30%. A therapeutically effective amount may also refer to the amount of an siNA sufficient to delay or minimize the onset of an eye disorder associated with IOP. A therapeutically effective amount may also refer to the amount of the therapeutic agent that provides a therapeutic benefit in the treatment or management of an eye disorder associated with elevated IOP. Further, a therapeutically effective amount with respect to an siNA of the invention means that amount of therapeutic agent alone, or in combination with other therapies, that provides a therapeutic benefit in the treatment or management of an eye disorder associated with increased IOP. Used in connection with an amount of an siRNA of the invention, the term can encompass an amount that improves overall therapy, reduces or avoids unwanted effects, or enhances the therapeutic efficacy of or synergizes with another therapeutic agent. Treatment with siNA alone or in combination should result in an IOP of about 14 and 20 mm Hg. However, any decrease in IOP as compared to pretreatment IOP is advantageous (e.g., a decrease in IOP greater that 5%, 10%, 25%, 30%, 35%, 40%, 50%, or 60% of pretreatment IOP).

A therapeutic benefit in the treatment or management of an eye disorder associated with increased IOP is the sustained decrease in IOP induced by the treatment. The more sustained the decrease is, the less likelihood there is of sudden sharp increases in IOP occurring when the next dose becomes due. This is considered a significant enhancement of the therapeutic efficacy. In some embodiments, treatment with siNA alone or in combination can result in a decrease in IOP sustained between about 2 days to about 7 days, between about 2 and about 6 days, and between about 2 days and about 4 days. In some preferred embodiment, the decrease is sustained between about 2 days and about 3 days, preferably during 3 days.

Consequently, in some embodiments administration of the compounds of the invention results in preventing, protecting against, or reducing the damage to the optic nerve caused by the reboot effect in IOP when the next dose becomes due in cases of patients' poor compliance with treatment schedules.

The effective amount and treatment regimen of a composition of the invention can be determined by standard research techniques. For example, the dosage of the composition which will be effective in the treatment, prevention or management of the disorder can be determined by administering the composition to an animal model such as, e.g., the animal models disclosed herein, e.g. the New Zealand white rabbit model, or known to those skilled in the art. In addition, in vitro assays may optionally be employed to help identify optimal dosage ranges. Alternatively, the dosage may be determined for an individual by titrating the dose until an effective level is reached.

Selection of the preferred effective amount to be used in dosages can be determined (e.g., via clinical trials) by a skilled artisan based upon the consideration of several factors which will be known to one of ordinary skill in the art. Such factors include the disorder to be treated or prevented, the symptoms involved, the patient's body mass, the patient's immune status and other factors known by the skilled artisan to reflect the accuracy of administered pharmaceutical compositions.

The precise dose to be employed in the formulation will also depend on the route of administration, and the seriousness of the disorder, and should be decided according to the judgment of the practitioner and each patient's circumstances.

When the siRNA is administered directly to the eye, generally an amount of between about 0.01 mg and about 100 mg per eye per day, between about 0.04 mg and about 80 mg per eye per day, between about 0.04 mg and about 20 mg per eye per day, between about 0.08 mg and about 10 mg per eye per day, between about 0.08 mg and about 1.2 mg per eye per day, between about 0.3 and about 0.9 mg per eye per day, or between about 0.08 mg and about 0.9 mg per eye per day, per day of siNA is administered. In preferred embodiments, the siRNA of the invention is administered in an amount of between about 0.08 mg and about 0.9 mg per eye per day, and between about 0.3 mg and about 0.9 mg, and between about 0.3 mg and about 0.6, and most preferably between about 0.6 mg and about 0.9 mg per eye per day. In a preferred embodiment the siRNA of the invention is formulated in a saline solution such as PBS. In a specifically preferred embodiment the siRNA of the invention is SYL040012 and is administered at the above defined doses. In some preferred embodiments, these doses may be administered once a day, twice a day, three times a day or four times a day, and the application to each eye is to take place daily, every other day, once a week, twice a week, three times a week, every other week, or once a month. In some embodiments the above doses may be administered at the same time each day or at different times each day. Given that pathologies characterized by increased IOP such as glaucoma are chronic in nature, in a preferred embodiment of the present invention the administration of the siNAs of the invention is also chronic. In alternative embodiments of the invention, where an increase in the patients' IOP is transitory the compositions of the invention shall be administered while the condition persists.

Formulations and Routes of Administration

The siNAs of the invention may be formulated into pharmaceutical compositions by any of the conventional techniques known in the art (see for example, Alfonso, G. et al., 1995, in: The Science and Practice of Pharmacy, Mack Publishing, Easton Pa., 19th ed.). Formulations comprising one or more siNAs for use in the methods of the invention may be in numerous forms, and may depend on the various factors specific for each patient (e.g., the type and severity of disorder, type of siNA administered, age, body weight, response, and the past medical history of the patient), the number and type of siNAs in the formulation, the form of the composition (e.g., in liquid, semi-liquid or solid form), the therapeutic regime (e.g. whether the therapeutic agent is administered over time once daily, several times a day or once every few days, and/or the route of administration).

In a preferred embodiment, the compositions of the invention are administered in the form of eye drops, delivered directly to the eye. The eye drops can be delivered in a volume of between about 10 µl and about 100 µl per drop, more preferably between about 20 µl and about 50 µl per drop, and most preferably between about 30 µl and about 33 µl per drop. In an additionally preferred embodiment the eyedrops are delivered in a volume of about 404 In a preferred embodiment the composition of the invention comprises SYL040012 in an acceptable solution such as PBS. In some preferred embodiments SYL040012 is administered once a day in eyedrops at a concentration of from about 7.5 mg/ml to about 22.5 mg/ml, preferably between about 15 mg/ml and 22.5 mg/ml.

These compositions can take the form of aqueous and non aqueous solutions, suspensions, emulsions, microemulsions, aqueous and non aqueous gels, creams, tablets, pills, capsules, powders, sustained-release formulations and the like. The siNAs of the invention can also be encapsulated in a delivery agent (including, but not limited to, liposomes, microspheres, microparticles, nano spheres, nanoparticles, biodegradable polymers, hydrogels, cyclodextrins poly(lactic-co-glycolic) acid (PLGA)) or complexed with polyethyleneimine and derivatives thereof (such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives). The preferred compositions of the invention are aqueous solutions, specifically preferred are saline solutions such as PBS, with a pH range of about 7.0 to about 7.4 preferably with a pH of 7.2±0.5.

Pharmaceutical carriers, vehicles, excipients, or diluents may be included in the compositions of the invention including, but not limited to, water, saline solutions, preferably buffered saline solutions, oils (e.g., petroleum, animal, vegetable or synthetic oils), starch, glucose, lactose, sucrose, gelatin, malt, rice, flour, chalk, silica gel, sodium stearate, glycerol monostearate, talc, sodium chloride, dried skimmed milk, glycerol, propylene, glycol, ethanol, biopolymers (e.g., carbopol, hialuronic acid, polyacrylic acid, etc.), dextrose, permeation enhancers (e.g., fatty acids, fatty acid esters, fatty alcohols and amino acids), and hydrophilic polymers (e.g., polycarbophil and polyvinylpyrolidone) and the like. The composition, if desired, can also contain minor amounts of wetting or emulsifying agents, or pH buffering agents.

Suitable lipophilic solvents or vehicles include fatty oils such as sesame oil, or synthetic fatty acid esters, such as ethyloleate or triglycerides, or liposomes. Optionally, the suspension may also contain suitable stabilizers or agents which increase the solubility of the compounds to allow for the preparation of highly concentrated solutions.

In preferred embodiments, the compositions of the invention are formulated in a solution, preferably a buffered saline solution such as PBS, or a gel for topical administration to the eye, such as, for example, in the form of eye drops. In such embodiments, the formulations may be cationic emulsions and/or contain biopolymers including, but not limited to, poly(lactide-co-glycolide), carbopol, hialuronic acid and polyacrylic acid.

In a specific preferred embodiment, the compositions of the invention are formulated in a solution such as phosphate-buffered saline (PBS), which may optionally also comprise one or more pharmaceutically acceptable diluents and or excipients such as benzalkonium chloride, which will allow ocular instillation on the corneal surface in the form of an eyedrop preferably of between about 30 and about 33 µl. In such preferred embodiments the dose administered is between about 0.6 mg and about 0.9 mg per eye per day, preferably administered once a day.

The siNAs of the present invention can also be formulated in combination with other therapeutic compounds that decrease IOP (e.g., commercially available drugs).

Kits

The siNA compounds of the invention can also be provided in kits that comprise a dispenser with an orifice for dispensing specific dosages of the siNA compound in a droplet of predetermined volume. In a preferred embodiment the siNA compounds of the invention are siNAs targeted against SEQ ID NO: 1. In a further preferred embodiment the dispensers within the kit of the invention provide a composition comprising SYL040012. In another embodiment the kit can comprise a collection of single use dispenser, for example for use during one month, in this specific case, the case would contain 30 single use dispensers. The droplet can range from about 50 μl to about 100 Win volume. The dispenser can be a single use dispenser and comprise between about 1 mg and about 2 mg of the siNA compounds of the invention, and optionally also comprise one or more pharmaceutically acceptable diluents, and optionally one or more excipients. The composition contained in the dispenser can comprise a concentration of between about 15 mg/ml to about 22.5 mg/ml of the siNA compound of the invention. Alternatively, the dispenser can be designed to be use for one month or more and the volumes contained will increase accordingly to provide the equivalent number of doses. The kits of the invention can also comprise instructions specifying that a dosage of the siNA compound of between about 0.6 mg and about 0.9 mg in 1 droplet is to be applied to each eye. The instructions can further specify that the droplets are applied to each eye once a day, twice a day, three times a day, or four times a day, and that the application to each eye is to take place daily, every other day, once a week, twice a week, three times a week, every other week, or once a month.

The contents of all published articles, books, reference manuals and abstracts cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Modifications and variations of the present invention are possible in light of the above teachings.

EXAMPLES

Example 1: In Vitro Analysis of SYL040012

Cell Culture and Transfections

BxPC3 and MDA-MB-231 cells were obtained from American Association of Culture Collection (Rockville, Md., USA) and maintained in culture medium (RPMI-1640 medium supplemented with 10% FBS (BxPC3 cells) and 10% FBS supplemented DMEM (MDA-MB-231 cells) in a humidified incubator under an atmosphere of 5% CO2/95% air at 37° C. For transfections cells were seeded at a density of 106.000 cells/cm2 for BxPC3 line and 200.000 cells/cm2 for MDA-MB-231 line. When cell cultures reached approximately 90% confluence, cells were transfected with 100 nM SYL040012 using Lipofectamine 2000 (Invitrogen, Pasley, UK). Transfection efficiency was estimated by quantifying the amount of Block-it-Alexa fluor red fluorescent oligonucleotide (Invitrogen, Pasley, UK) present inside cells in control cultures 24 h after transfection.

RNA Isolation and qReal Time-PCR

Total RNA was isolated from cell cultures or tissues using RNeasy RNA extraction kit (Invitrogen, CA, USA). 4 μg of total RNA were retrotranscribed using High-Capacity cDNA Archive kit (Applied Biosystems, Inc., Foster City, Calif., USA) according to the manufacturer's instructions.

Real time PCR was performed using Stepone plus detection system (Applied Biosystems). 500 nanograms of each sample were amplified in a TaqMan 2× Universal Master Mix under the following conditions: 95° C. for 10 min, followed by 40 cycles of 95° C. for 15 s and 60° C. for 1 min. All real time qRT-PCR amplifications were performed in triplicate and repeated in five independent experiments, always including reverse transcription controls and no template controls.

ADRB2 mRNA levels were analyzed by qRT-PCR at different time points after transfection with 100 nM SYL040012 (24, 48 and 72 hours) according to the above described protocol. Quantification data of ADRB2 gene were normalized to HPRT1 expression in rabbit cells and tissues and to GAPDH expression in human cells which served as a positive amplification control.

Cell Viability Assays

Cell viability was assessed by the MTT method and assayed at different time-points (24, 48 and 72 hours) after transfection in MDA-MB-231 and BxPC3 using the Cell Titer 96 Aqueous Non Radioactive Cell Proliferation Assay kit (Promega, Mannheim, Germany) following the manufacturer's instructions.

In Vitro Analysis of Efficacy, Specificity and Safety of SYL040012

Figure 1A:
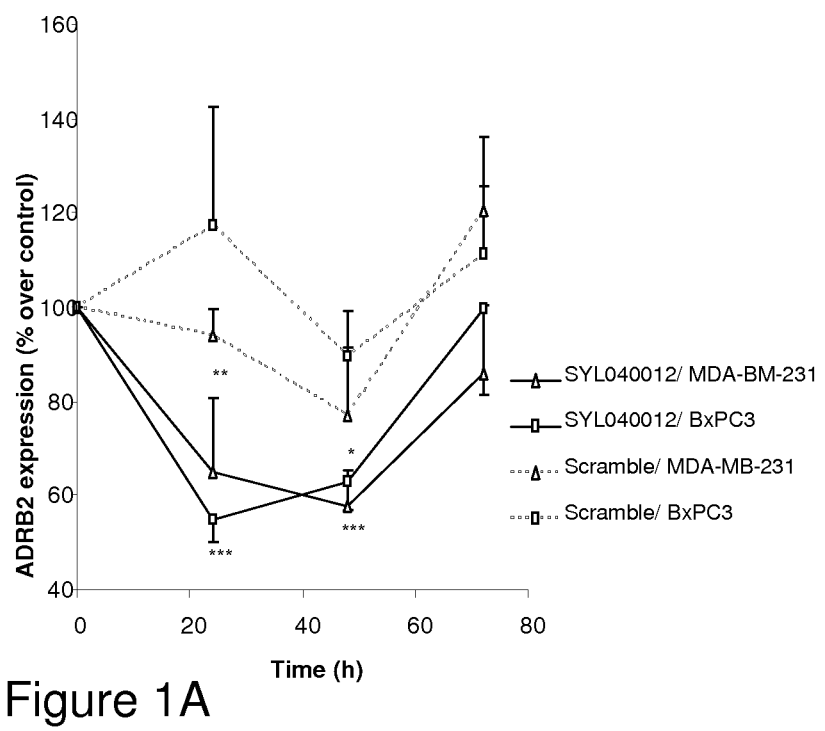
FIG. 1: In vitro efficacy of SYL040012 in human cells. (A) Time course inhibition of ADRB2 in human cells: BxPC3 and MDA-MB-231 cells were transfected with either 100 nM of SYL040012 or 100 nM of a scramble sequence siRNA, RNA was extracted and expression of ADRB2 was analysed at different time-points after transfection. (B) Dose-dependent inhibition of ADRB2 in response to SYL040012 in BxPC3 cells: BxPC3 cells were transfected with increasing doses of SYL040012 and ADRB2 expression was analysed 48 h after transfection. (C) Expression of the adrenergic family receptors in response to SYL040012.

ADRB2 mRNA levels were analyzed by qPCR at different time points (24, 48 and 72 hours) after transfecting cell cultures of BxPC3 or MDA-MB-231 with either 100 nM of SYL040012 or a scramble siRNA. A reduction that varied between 50-70% of basal mRNA levels of ADRB2 was observed, depending on the time-point (FIG. 1A). In both cell lines, maximal effect of SYL040012 was observed 24 h after transfection, at this time point the reduction in ADRB2 mRNA was approximately 50% of basal levels. In BxPC3 cells basal ADRB2 levels were recovered approximately 72 h post-transfection, whereas in MDA-MB-231 cells mRNA levels at this point remained below basal line. Transfection of a scramble RNA sequence did not modulate ADRB2 levels demonstrating that effect the SYL040012 was specific.

In order to assess if the reduction in ADRB2 levels had an effect on cell viability a MTT assay was performed at the same time points mentioned above. SYL040012 did not cause any significant effect on cell viability over time (Table 1). This result indicates that the ADRB2 mRNA reduction in response to SYL040012 does not cause cell toxicity.

TABLE 1

Cell viability in MDA-MB-231 and BxPC3 cells following treatment with
either 100 nM SYL040012, 100 nM of a scramble sequence or PBS. Cell viability was
analyzed using an MTT assay 24, 42 and 72 h after treatment with 100 nM SYL040012,
the same dose of scramble sequence siRNA or vehicle. Data represent means ± s.e.m of
three independent experiments.

| Time | MDA-MB-231 | | | BxPC3 | | |
|---|---|---|---|---|---|---|
| (h) | SYL040012 | Scramble | Control | SYL040012 | Scramble | Control |
| 24 | 96.39 ± 5.41 | 107.13 ± 2.43 | 100.00 ± 12.54 | 113.22 ± 8.20 | 108.62 ± 24.19 | 100.00 ± 13.79 |
| 48 | 105.70 ± 0.63 | 101.71 ± 2.96 | 100.00 ± 1.59 | 97.15 ± 0.16 | 107.29 ± 2.74 | 100.00 ± 3.22 |
| 72 | 105.86 ± 12.56 | 112.87 ± 9.18 | 100.00 ± 7.08 | 99.75 ± 15.62 | 101.33 ± 2.96 | 100.00 ± 5.57 |

Figure 1B:
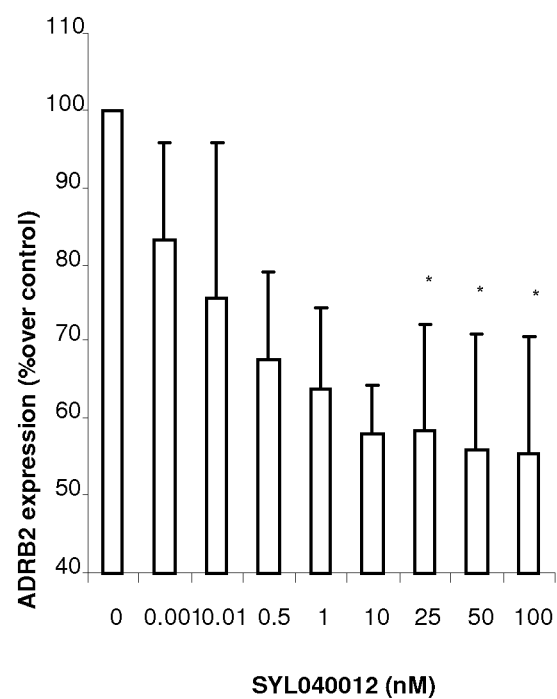

Compounds based on RNAi depend on the activity of endogenous RNAi machinery. One of the pitfalls of RNAi is that this endogenous system can be saturated when big amounts of exogenous RNA molecules are added[22]. With the aim of assessing the effect of different doses of SYL040012, BxPC3 cells were transfected with increasing doses of SYL040012 (0.001 to 100 nM). Total RNA was isolated 24 hours after transfection and ADRB2 mRNA levels were determined by real-time PCR (FIG. 1B). A statistically significant reduction in ADRB2 levels was observed at a 0.5 nM dose. Maximum effect was seen in response to a of 10 nM dose. No significant differences were observed between the concentrations of 10 and 100 nM. Using these data, the inhibitory concentration 50 (IC50) value was calculated to be 9.2 nM.

Figure 1C:
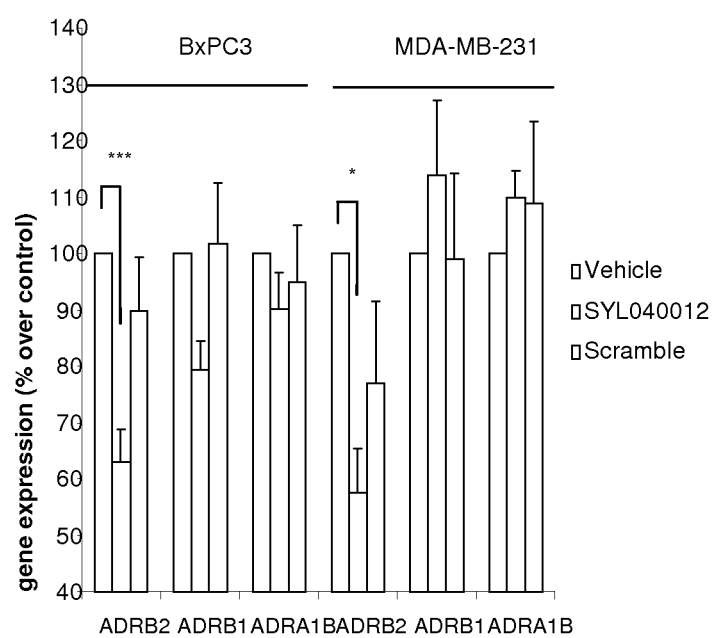

Specificity of a compound for its target is crucial for reduction of side effects in the clinical setting. We analysed the effect of SYL040012 on receptors of the adrenergic family to analyse its effect on the mRNA of proteins that are structurally related to ADRB2. mRNA levels of adrenergic receptors ADRB2, ADRB1, and ADRA1B were assessed in BxPC3 cells after treatment with SYL040012. FIG. 1C shows that SYL040012 was able to selectively decrease ADRB2 levels mRNA without significantly affecting mRNA levels of ADRB1 or ADRA1B.

Example 2: Stability Studies

Methods

Stability of SYL040012 in rabbit serum and rabbit aqueous humour was assessed by two methods: a native HPLC method to measure the quantity of duplex RNA by separating double-stranded RNA from non-hybridized single-strands, and a denaturing IEX-HPLC method to evaluate purity of both single strands in the duplex and to detect potential degradation compounds in order to evaluate the stability of the single strands. Additional tests such as appearance, pH and UV measurement were made according to current editions of European and US Pharmacopeias.

Stability of SYL040012

RNA compounds are very easily degraded by RNAses, for this reason the stability of the compound was assessed in its vehicle (PBS), in rabbit serum and in rabbit aqueous humor.

The results of the stability study of SYL040012 drug product upon incubation for up to 24 hours at 37° C. in rabbit serum and rabbit aqueous humor are shown in FIG. 2. These results demonstrate that SYL040012 half-life is above 24 hours in rabbit aqueous humor whereas the half life in rabbit serum is below 30 minutes.

Example 3: siRNA Biodistribution in the Eye of GFP Mice

Methods

C57BL/6-Tg (ACTbEGFP) adult male rabbits of approximately 8 weeks were used for the study. Mice were housed in groups and kept in a controlled-temperature room with a 12 h light/dark cycle and free access to food and water.

Eyes of 6-8 weeks old eGFP transgenic mice were treated with a dose of 11.2 nmol/day of eGFP-siRNA over a period of three consecutive days. This model has been extensively described in literature.sup.34 and expresses eGFP protein abundantly, which is easily detected by fluorescence. RNAi target sequence used was as follows: EGFP 5'-GGCTACGTCCAGGAGCGCACC-3' (SEQ ID NO:7). 48 h after the last application, animals were sacrificed and both eyes collected and processed for fluorescence microscopy.

siRNA Biodistribution in Green Fluorescent Protein (GFP) Transgenic Mice

An important first step in any interference study is to optimize conditions of siRNA delivery in vivo. The ability to detect phenotypic changes or loss of function in a target population depends on the efficiency with which the siRNA is delivered into target tissue.

In order to investigate whether siRNAs can pass through the cornea and access the anterior chamber of the eye, a green fluorescent protein specific siRNA was assayed in eGFP transgenic mice. The application of a siRNA specifically designed for eGFP, diminished fluorescence in the ciliary processes and trabecular meshwork when compared to untreated mice (FIG. 3). This result indicates that, on the one hand the siRNA can access the anterior chamber of the eye and, on the other hand, once there, it is taken up by the cells of the ciliary processes and is capable of reducing the expression of the target gene.

Example 4: In Vivo Efficacy

Animals

Adult male New Zealand White Rabbits (NZW) (Granja San Bernardo, Spain and Charles River Laboratories) of approximately 10 weeks were used for all experiments. Animals were individually housed in standard cages in a controlled-temperature room with a 12 h light/dark cycle with free access to food and water. Animals were subjected to a basic ophthalmic examination during the week prior to the beginning and at the end of each study. The following parameters were observed: eyelid irritation/inflammation, tear production, pupil size, cornea appearance and conjunctive irritation/inflammation.

All animals were handled according to the ARVO statement for use of Animals in Ophthalmic and Vision Research.

IOP Measurement

IOP was measured using the Applanation Tonometer TONO-PEN AVIA™ after topical application of Colircusí® anestésico (0.4% tetracaine+0.4% oxibuprocaine, Alcon) to the cornea, to avoid animal discomfort. Every measurement was performed by triplicate and average results are shown.

Oral Water-Loading Hypertension Model

Four days prior to beginning each study five IOP measurements were registered with 2 h intervals between measurements. Animals were thereafter assigned to experimental groups randomizing the animals according to IOP values. Compounds were instilled on into the eye once a day over a period of 4 days in a dose volume of 40 µL per eye containing 20 nmol of siNA in PBS. PBS was used as a negative control. During the first three days of administration basal IOP measurements were recorded prior to test item or vehicle administration. IOP was measured 4 times post-administration with a 2 hour-interval.

On the fourth day of study, basal IOP measurements were recorded prior to administration and 1 and 2 hours post-administration. At this point hypertension was induced by means of oral water-loading (60 mL/kg) in overnight fasted animals. Thereafter, IOP was measured a total of 10 times with a 25 minute-interval between measurements. After the last measurement, animals were euthanized by an overdose of pentobarbital and the main ocular structures were collected and preserved in RNA later until processing.

In Vivo Efficacy of SYL040012

As a first step to demonstrate in vivo efficacy of SYL040012 New Zealand White Rabbits were treated with three of the products that are currently first-line treatment for glaucoma: TRUSOPT™ (dorzolamide), XALATAN™ (latanoprost) and Timoftol (timolol). A single drop (40 µL) of each of the compounds was instilled into the eyes of three separate groups of rabbits over a period of four consecutive days. IOP measurements were obtained every hour for 8 hours, starting one hour after the last administration. All compounds caused an IOP reduction of between 20-35%, depending on the compound, and this effect lasted approximately 6 hours (data not shown). These experiments confirmed the suitability of this animal model due to its ability to respond to IOP regulators.

Figure 4A:
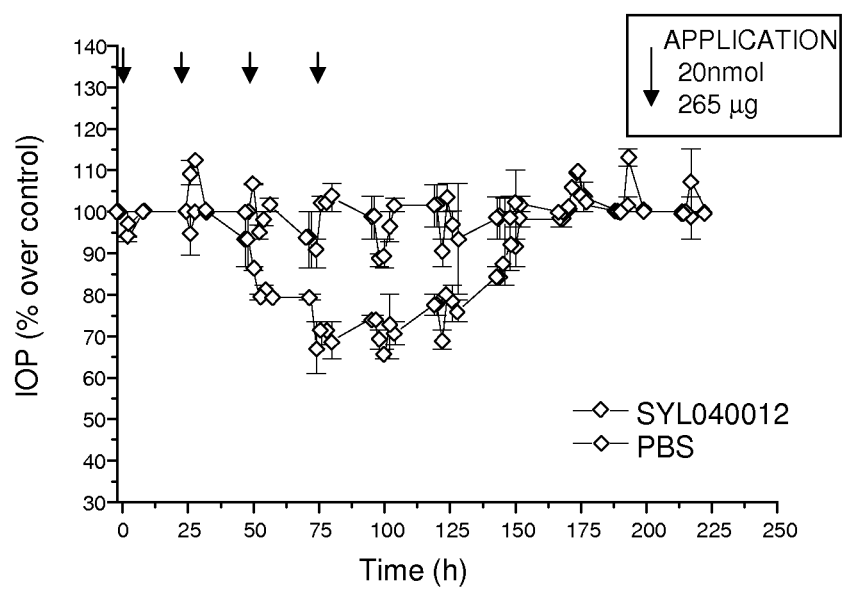
Figure 4B:
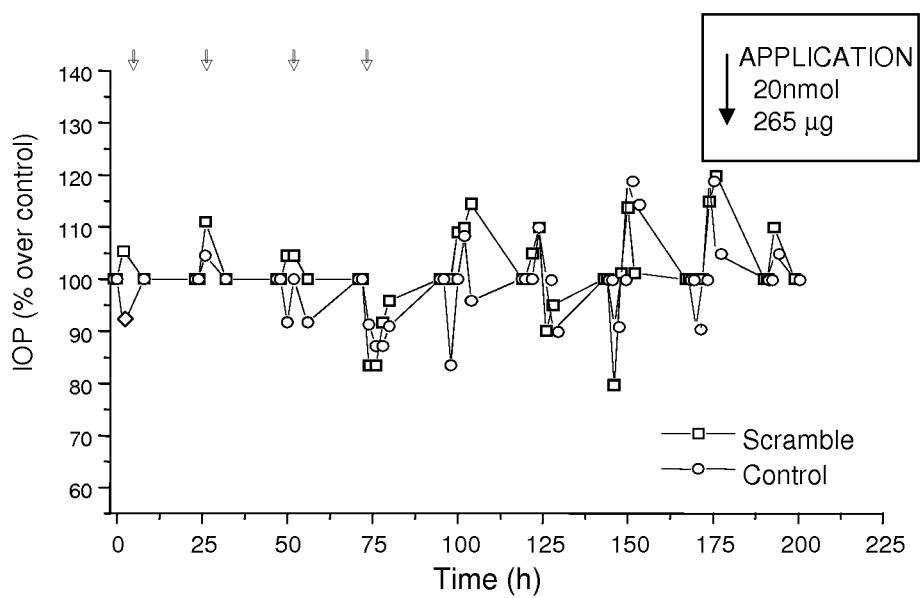

To assess the effect of SYL040012 on IOP, New Zealand White rabbits were instilled with either 0.3 mg/day of SYL040012 or PBS over a period of 4 consecutive days, in the form of one 40 µl eyedrop per day. FIG. 4A shows that there was an IOP reduction of 21.81%±1.55% when compared to the control group instilled with vehicle. The effect of SYL040012 on IOP was detectable after two days of treatment and the values remained below basal levels until approximately two days after the last application. Specificity of the effect was assessed by performing the same experiment administering a scramble sequence instead of the compound. The results, shown in FIG. 4B, indicate that scrambled siRNA had no effect on IOP, thus the effect of SYL040012 was specific.

The mean time effect of SYL040012 was calculated as the difference between the half maximal time-point of recovery and the time at which the half maximal effect on IOP was achieved. The results of these calculations are shown in Table 3, and illustrate the difference in mean time effect of SYL040012 (91.6 h) versus XALATAN™ (5.36 h) and TRUSOPT™ (4.75 h).

Figure 4C:
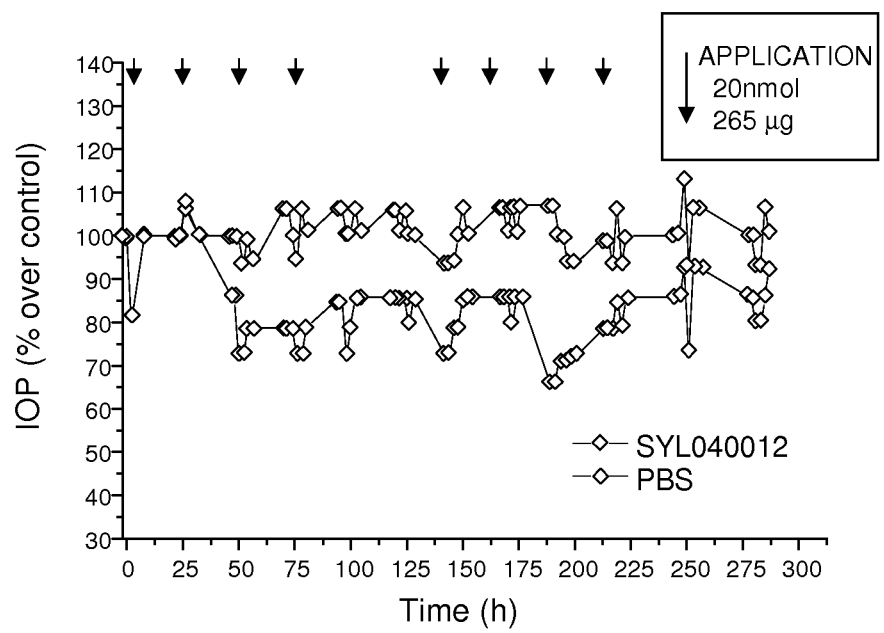

In order to analyze the effect of SYL040012 over time, a group of rabbits received two sets of four once a day applications of the compound at a dose of 0.3 mg/day, separated from each other by a drug free period of three days. FIG. 4C shows that there was an IOP reduction of 19.29±0.89% and that this decrease in IOP was maintained over time. Reduction in IOP was observed from the second application until approximately 48 h after the last application, including during the three-day drug free period. The fact that SYL040012 is able to maintain the reduction in IOP levels in this animal model even when the compound is not administered for a period of up to 72 hours is very attractive. When commercial drugs are used, sustained reduction of IOP relies on the continuous application of the drugs. This latter feature suggests that SYL040012 can protect against the eventual optic damage caused by a reboot effect in IOP in case of patients' poor compliance with the treatment.

Example 5: In Vivo Efficacy in an Animal Model with Ocular Hypertension

To evaluate the IOP-lowering effect of SYL040012 in conditions closer to pathological conditions observed in glaucoma, an oral water overloading model in New Zealand White Rabbits was used. This model has previously been described by several authors[35-38]. The main advantage of this model over other experimental models of ocular hypertension is that administration of irritant compounds or techniques that are traumatic to the eye are avoided, leaving ocular structures intact. This allows the eye to respond normally to test drugs[38].

Figure 5A:
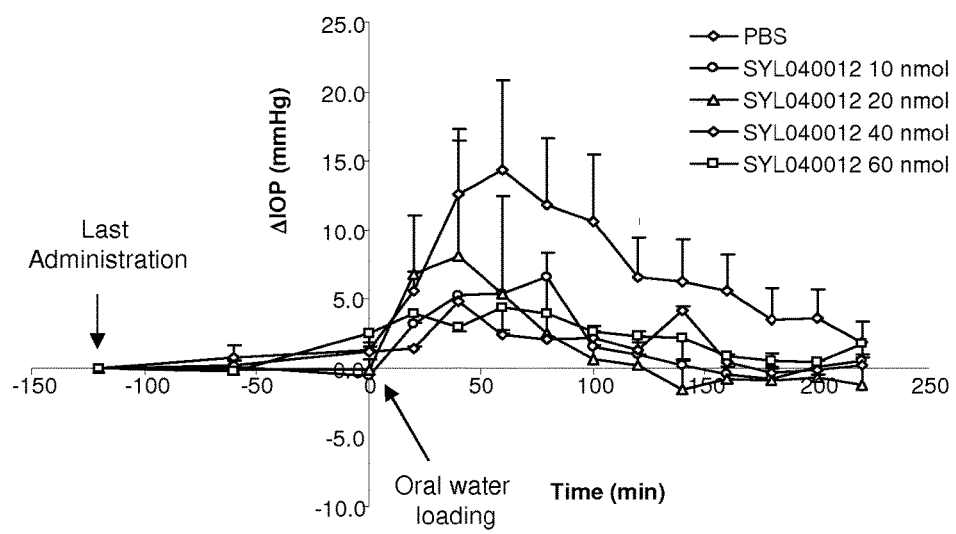

The first experiment was a dose-range finding in which four different doses of SYL040012 (0.15, 0.3, 0.6 and 0.9 mg/eye/day) were administered a total of 3 times: 48, 24 and 2 hours before hypertension induction. All treatments were applied in both eyes and IOP was measured before hypertension induction and every 20 minutes up to 120 minutes after oral overloading. A repeated measures two-way ANOVA analysis of the results showed a statistically significant effect of both time ($p<0.001$) and treatment ($p<0.0001$) but no interaction between these factors. Differences between each of the doses and PBS were analyzed using a one-way ANOVA with a Dunnett's post-hoc test. FIG. 5A shows that SYL040012 provides significant protection against the rise of IOP at all doses tested ($p<0.01$ vs saline in all cases). The maximum mean ΔIOP value (IOP after water-loading IOP before water-loading) in animals treated with SYL040012 was 6.6 mmHg, 8.2 mmHg, 4.8 mmHg and 4.3 mm Hg for doses of 0.15, 0.30, 0.60 and 0.90 mg/day/eye respectively vs a maximum ΔIOP in control animals (treated with vehicle) of 15.55 mmHg.

Figure 5B:
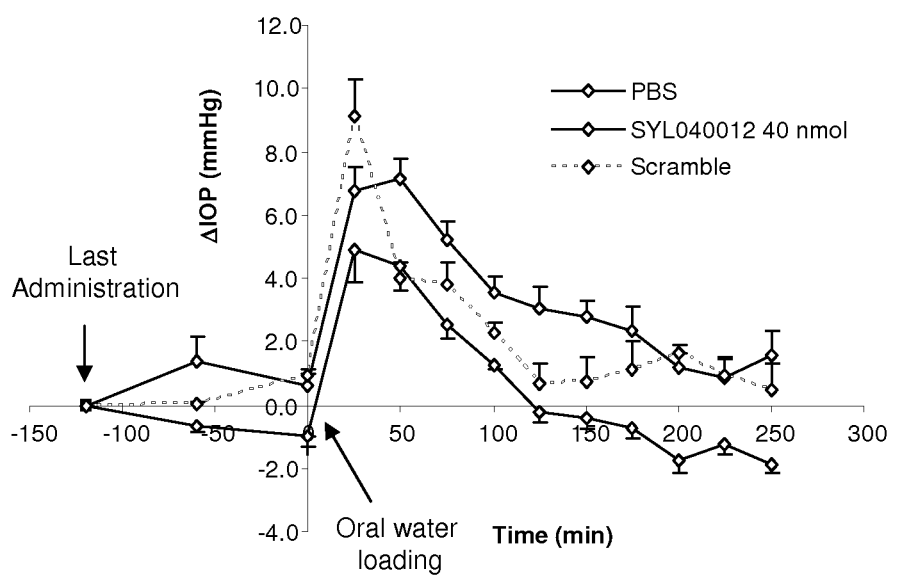
Figure 5C:
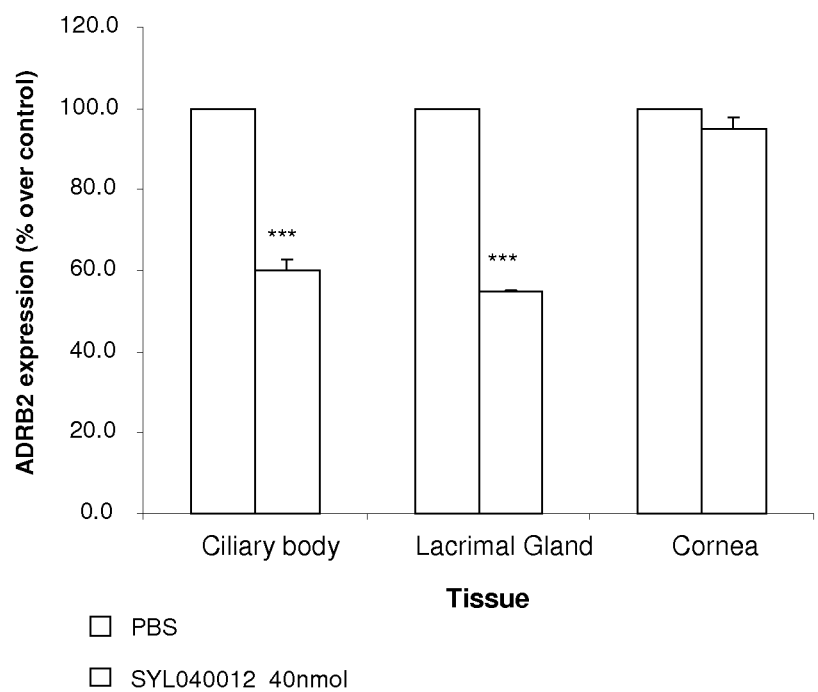

In order to confirm the efficacy and specificity of SYL040012 on IOP a larger group of animals was treated with a fixed dose of 0.3 mg/day over a period of four consecutive days. As seen in FIG. 5B, water loading caused an increase in IOP of approximately 7 mmHg during the first hour after hypertension induction in animals treated with PBS. The repeated measures two way-ANOVA analysis of the results, show a significant effect of both time and treatment ($p<0.0001$ in both cases) but no interaction between these factors. Further analysis was performed by a one-way ANOVA with a Dunnett's post-hoc test for single comparisons. The results of this analysis show that treatment with SYL040012 significantly reduced the ΔIOP value within the first hour compared to PBS treated animals ($p<0.05$ vs. PBS). The effect of SYL040012 was specific since treatment with a scramble sequence siRNA had no effect on IOP ($p>0.05$ vs. PBS).

To further ensure that the observed decrease on IOP was a reflection of a corresponding decrease in the levels of ADRB2 mRNA, the relevant tissues were analyzed. Animals were treated as described above were sacrificed immediately after the last IOP measurement, eyes were enucleated and cornea, lacrimal gland and ciliary body were isolated. Total RNA was extracted and expression of ADRB2 was analyzed by real time PCR as described supra. As may be seen in FIG. 5C, a significant decrease in ADRB2 mRNA levels was observed in both ciliary body and lacrimal gland.

Example 6: SYL040012 in Humans

Subjects

Thirty healthy volunteers who had an IOP below 21 mmHg, Snellen visual acuity of 20/25 or better and who were at least 18 years of age were recruited. All subjects completed the study according to the protocol. The mean±standard deviations of the subjects' demographic parameters are shown in Table 1. A comprehensive physical examination and an ocular examination were performed before admittance into the study to assure the suitability of the subjects for participation in the study.

Study Design

A single-center, parallel, controlled, open-label phase I clinical study was designed to evaluate safety, tolerability, and bioavailability of SYL040012 administered as eye drops. An additional aim of the study was to determine the effect of different doses of SYL040012 on IOP. In all cases, the drug was instilled in one randomly chosen eye only; the fellow eye remained untreated and served as a control for ocular tolerance and safety. Both eyes were monitored in a blinded fashion.

Treatment Schedule

To minimize the risk of adverse effects and in accordance with the Guidelines on Strategies to Identify and Mitigate Risks for First-in-Human Clinical Trials with Investigational Medicinal Products (EMEA/CHMP/SWP/28367/07), the intervention phase was divided into two intervals. Interval 1 began with instillation of a single dose of SYL040012 to one subject who was observed for 72 hours. Tolerability was assessed at 24, 48, and 72 hours after instillation; when the tolerability criterion was met 72 hours after instillation, the next subject was dosed. The same procedure was followed for each new subject until six subjects had been administered. Good tolerance and thus the possibility of including the next volunteer was defined as an absence of grade 3 or higher toxicity on the Common Terminology Criteria for Adverse Events v3.0 scale.14 Safety and tolerability were assessed before interval 2 began.

During interval 2 SYL040012 was administered in daily instillations over 7 consecutive days. Two doses were assayed in this interval, each of which was administered to 12 subjects. For safety reasons, an initial group of three subjects received the low dose (600 μg) of SYL040012; when the tolerability criterion previously described was met, the remaining subjects assigned to this dose were administered. The same procedure was performed for the high dose (900 μg).

All subjects were treated in the Clinical Investigation Unit of the hospital, which guaranteed protocol compliance. Table 2 shows the flow chart diagram.

IOP Measurements

During interval 1, IOP was measured 1, 2, 4, 48, and 72 hours after instillation using Goldmann tonometry with the subjects sitting. During interval 2, the IOP curves were determined before the first instillation (screening) and after 4 days of treatment. In both cases, IOP was measured at 9:00, 12:00, 15:00, 18:00, and 21:00 hours. IOP was also measured every time ocular tolerance was assessed during intervals 1 and 2, 1 hour before and after instillation. Measurements performed outside of an IOP curve were taken in the morning between 9:00 and 12:00.

Statistical Analysis

Ocular and conjunctival local tolerance after SYL040012 treatment was assessed by analyzing occurrence and frequency of ocular adverse effects 72 hours after instillation for interval 1 and 24 hours after the last instillation during interval 2. Comparisons were made between eyes (administered vs. non-administered) using the chi-squared test. Analysis of single daily IOP values after one instillation was performed by comparing values obtained after SYL040012 instillation to the basal value at screening. Statistical significance was assessed by paired Student's t test. The effect of SYL040012 on IOP during interval 2 was assessed by comparing the IOP curve obtained at day 4 to the one obtained at screening. Statistical significance was assessed by repeated measures two-way analysis of variance (ANOVA), using treatment and time of day as variables and IOP as the repeated measure followed by a Bonferroni post-hoc test to assess the significance at each time point. Other parameters (clinical analysis, visual acuity, symptom duration) were analyzed using paired Student's t tests or Wilcoxon test depending on compliance of the conditions required for using each of these statistical tests. P<0.05 was considered significant.

Results: Effect of SYL040012 on IOP

Figure 6A:
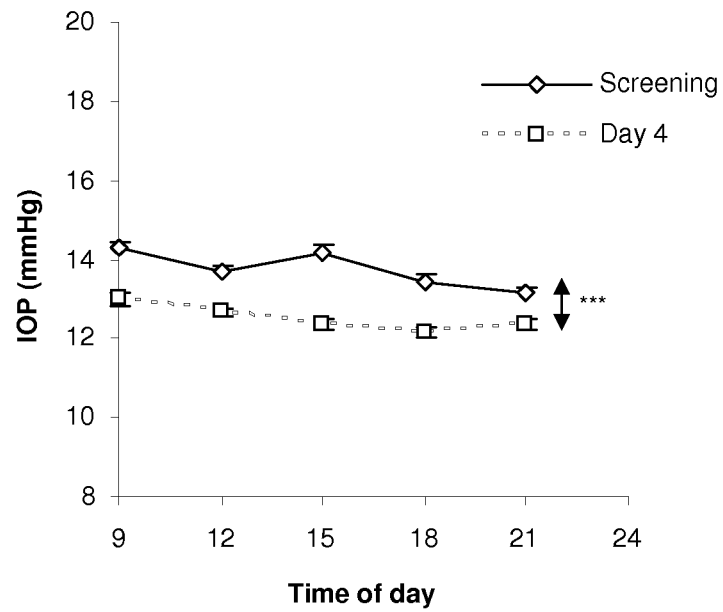
Figure 6B:
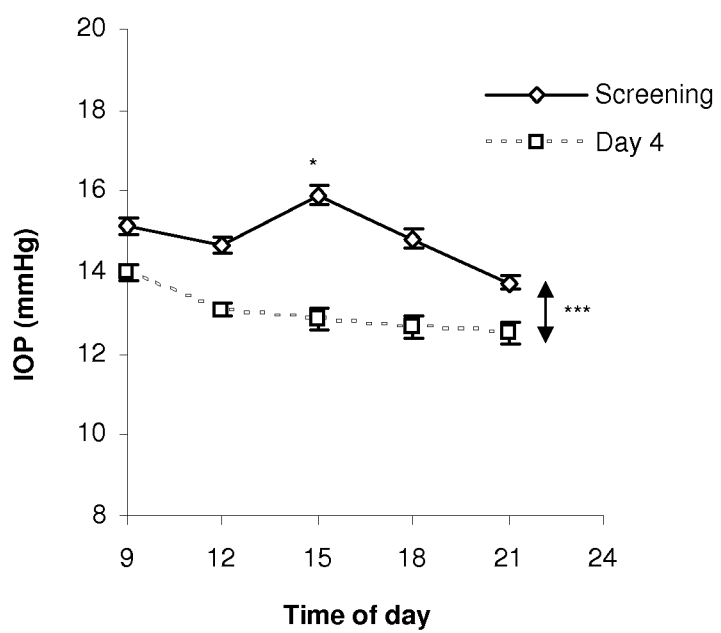

No significant differences in IOP were seen between the values obtained at screening and those obtained following a single instillation of SYL040012. During interval 2, administration of SYL040012 on a repeated dose schedule over a period of 7 days reduced IOP values in 15 out of 24 healthy subjects regardless of the dose used. The 600 μg dose of SYL040012 caused an overall statistically significant decrease in IOP after 4 days of administration; the post hoc data analysis showed a significant effect of SYL040012 on the measurements obtained at 15:00 hours (FIG. 6A). Five volunteers who received this dose showed a mean reduction in IOP values exceeding 20% on day 4 compared to values at screening. We performed a separate analysis in this subgroup and found an overall statistically significant effect on IOP; the post hoc analysis revealed that the differences were statistically significant at all time-points studied (FIG. 6B). It is noteworthy that the basal IOP value in these five subjects was higher than the basal IOP values in other subjects (16.2±2.9 mmHg vs. 14.9±2.8 mmHg, respectively). This increased responsiveness with higher IOP values has been reported for other antiglaucoma drugs.[39]

Example 7: Treatment of Ocular Hypertension or Open-Angle Glaucoma in Adults: A Double-Blind, Placebo Controlled, Multiple-Dose Efficacy Trial Patients A total of 80 male and female subjects in good or fair general health as assessed by the investigator, aged ≥18 years, with a previous history or newly diagnosed elevated IOP (≥21 mmHg) with or without open-angle glaucoma in both eyes are recruited. To be included in this study they must have a normal result, or result typical for open-angle glaucoma of the following assessments in both eyes:

Visual field 24-2 or equivalent (24-2 Humphrey visual field SITA test, about 5 minutes per eye).
Optical coherence tomography (OCT).
Best corrected visual acuity ≥0.5 (20/40) on the Snellen chart, or ≤0.3 log MAR.
Schirmer test (lacrimation)
Funduscopy. .

The main objective of this trial is to determine tolerability on the ocular surface (cornea and conjunctiva) and effect on intraocular pressure after a daily dose of SYL040012 during 14 days of treatment.

Secondary objectives include assessment of local tolerability after each dose, systemic tolerability (effect on laboratory parameters, physical examination, vital signs and electrocardiogram), and changes (if any) of the ocular fundus or visual acuity possibly related to the investigational product.

Baseline Period

Up to 30 days before the first administration of the investigational product subjects are enrolled for eligibility to participate in the Treatment Period of the clinical trial. If an anti-glaucoma medication requires washout, this period may be longer. Temporary prescription of anti-glaucoma medication requiring a short wash-out is allowed. If at the beginning of the baseline period the patient is on an anti-glaucoma medication with several weeks wash-out (cf. European Glaucoma Society, footnote to the study Flow Chart), the investigator may prescribe another anti-glaucoma medication with a short wash-out time in order to avoid the eyes being without IOP-lowering medication for several weeks.

Treatment Period

On Day 1 subjects are randomised to 80 µg SYL040012, 300 µg SYL040012, 900 µg SYL040012 or placebo in a ratio of 1:1:1:1 to be administered in eyedrops.

Subjects return each day (including bank holidays and weekends) to the site for investigational product administration and assessments. Subjects receive 1 dose of the investigational product once daily in both eyes for 14 days.

Follow-Up Visit

The final assessment will be done at the follow-up visit which takes place 4 to 7 days after the last investigational product administration (from 96 hours after the last administration [4 days]+3 days).

To determine the effect of SYL040012 on patients' IOP, a 24-hour curve of IOP measurements is obtained with a Goldmann tonometer the day before beginning treatment, and on day 14. Time points are adjusted to a classical timetable for IOP curve measurements (09:00, 12:00, 15:00 and 18:00 and at 9:00 next day). Furthermore single IOP measurements are performed on day 1, 7 and 15, and also during the follow up visit which takes place between 4 and 7 days after receiving the last administration.

REFERENCES CITED IN THE TEXT

1. Quigley H. Glaucoma. *Lancet* 2011; 377:1367-1377.
2. Weinreb R N, Khaw P T. Primary open-angle glaucoma. *Lancet* 2004; 363:1711-1720.
3. Glaucoma is the second leading cause of blindness globally. *Bulletin of the World Health Organization* 2004; 82:811-890.
4. Varma R, Lee P P, Goldberg I, Kotak S. An assessment of the health and economic burdens of glaucoma. Am J Ophthalmol 152:515-522.
5. Khaw P T, Shah P, Elkington A R. Glaucoma—1: diagnosis. *BMJ* 2004; 328:97-99.
6. Caprioli J, Varma R. Intraocular pressure: modulation as treatment for glaucoma. *Am J Ophthalmol* 152:340-344 e342.
7. Heijl A, Leske M C, Bengtsson B, Hyman L, Hussein M. Reduction of intraocular pressure and glaucoma progression: results from the Early Manifest Glaucoma Trial. *Arch Ophthalmol* 2002; 120:1268-1279.
8. Khaw P T, Shah P, Elkington A R. Glaucoma—2: treatment. *BMJ* 2004; 328:156-158.
9. Han J A, Frishman W H, Wu Sun S, Palmiero P M, Petrillo R. Cardiovascular and respiratory considerations with pharmacotherapy of glaucoma and ocular hypertension. *Cardiol Rev* 2008; 16:95-108.
10. Alm A, Camras C B, Watson P G. Phase III latanoprost studies in Scandinavia, the United Kingdom and the United States. *Surv Ophthalmol* 1997; 41 Suppl 2:S105-110.
11. Servat J J, Bernardino C R. Effects of common topical antiglaucoma medications on the ocular surface, eyelids and periorbital tissue. *Drugs Aging* 28:267-282.
12. De Natale R, Le Pen C, Berdeaux G. Efficiency of glaucoma drug regulation in 5 European countries: a 1995-2006 longitudinal prescription analysis. *J Glaucoma* 20:234-239.
13. Kass M A, Heuer D K, Higginbotham E J, et al. The Ocular Hypertension Treatment Study: a randomized trial determines that topical ocular hypotensive medication delays or prevents the onset of primary open-angle glaucoma. *Arch Ophthalmol* 2002; 120:701-713; discussion 829-730.
14. Singh K, Shrivastava A. Medical management of glaucoma: principles and practice. Indian J Ophthalmol; 59 Suppl:S88-92.
15. Gupta S K, Agarwal R, Galpalli N D, et al. Comparative efficacy of pilocarpine, timolol and latanoprost in experimental models of glaucoma. Methods Find Exp Clin Pharmacol 2007; 29(10): 665-71.
16. Servat J J, Bernardino C R. Effects of common topical antiglaucoma medications on the ocular surface, eyelids and periorbital tissue. Drugs Aging; 28(4):267-82.
17. Han J A, Frishman W H, Wu Sun S, Palmiero P M, Petrillo R. Cardiovascular and respiratory considerations with pharmacotherapy of glaucoma and ocular hypertension. *Cardiol Rev* 2008; 16:95-108.
18. Nieminen T, Lehtimaki T, Maenpaa J, Ropo A, Uusitalo H, Kahonen M. Ophthalmic timolol: plasma concentration and systemic cardiopulmonary effects. *Scand J Clin Lab Invest* 2007; 67:237-245.
19. Zimmerman T J. Topical ophthalmic beta blockers: a comparative review. *J Ocul Pharmacol* 1993; 9:373-384.
20. Wax M B, Molinoff P B. Distribution and properties of beta-adrenergic receptors in human iris-ciliary body. *Invest Ophthalmol Vis Sci* 1987; 28:420-430.
21. Elena P P, Denis P, Kosina-Boix M, Saraux H, Lapalus P. Beta adrenergic binding sites in the human eye: an autoradiographic study. *J Ocul Pharmacol* 1990; 6:143-149.
22. Elena P P, Kosina-Boix M, Moulin G, Lapalus P. Autoradiographic localization of beta-adrenergic receptors in rabbit eye. *Invest Ophthalmol Vis Sci* 1987; 28:1436-1441.
23. Trope G E, Clark B. Beta adrenergic receptors in pigmented ciliary processes. *Br J Ophthalmol* 1982; 66:788-792.
24. Lu P Y, Xie F, Woodle M C. In vivo application of RNA interference: from functional genomics to therapeutics. *Adv Genet* 2005; 54:117-142.
25. Lopez-Fraga M, Martinez T, Jimenez A. RNA interference technologies and therapeutics: from basic research to products. *BioDrugs* 2009; 23:305-332.
26. Behlke M A. Progress towards in vivo use of siRNAs. Mol Ther 2006; 13(4):644-70.

27. Lu S, Cullen B R. Adenovirus VA1 noncoding RNA can inhibit small interfering RNA and MicroRNA biogenesis. *J Virol* 2004; 78(23):12868-76.
28. Miller V M, Gouvion C M, Davidson B L, Paulson H L. Targeting Alzheimer's disease genes with RNA interference: an efficient strategy for silencing mutant alleles. *Nucleic Acids Res* 2004; 32(2):661-8.
29. Nguyen Q D, Schachar R A, Nduaka C I, et al. Phase 1 dose-escalation study of a siRNA targeting the RTP801 gene in age-related macular degeneration patients. *Eye (Lond)* 2012.
30. DeVincenzo J, Lambkin-Williams R, Wilkinson T, et al. A randomized, double-blind, placebo-controlled study of an RNAi-based therapy directed against respiratory syncytial virus. *Proc Natl Acad Sci USA* 2010; 107(19):8800-5.
31. Behlke M A. Progress towards in vivo use of siRNAs. *Mol Ther* 2006; 13:644-670.
32. Campochiaro P A. Potential applications for RNAi to probe pathogenesis and develop new treatments for ocular disorders. *Gene Ther* 2006; 13:559-562.
33. Elbashir S M, Lendeckel W, Tuschl T. RNA interference is mediated by 21- and 22-nucleotide RNAs. *Genes Dev* 2001; 15:188-200.
34. Ma D F, Tezuka H, Kondo T, et al. Differential tissue expression of enhanced green fluorescent protein in 'green mice'. *Histol Histopathol* 2010; 25:749-754.
35. Gupta S K, Agarwal R, Galpalli N D, Srivastava S, Agrawal S S, Saxena R. Comparative efficacy of pilocarpine, timolol and latanoprost in experimental models of glaucoma. *Methods Find Exp Clin Pharmacol* 2007; 29:665-671.
36. Hariton C, Marce D, Debon C. Transitory models of experimentally induced intraocular pressure changes in the rabbit. A reappraisal. *J Pharmacol Methods* 1990; 24:79-88.
37. Bonomi L, Tomazzoli L, Jaria D. An improved model of experimentally induced ocular hypertension in the rabbit. *Invest Ophthalmol* 1976; 15:781-784.
38. Santafe J, Martinez de Ibarreta M J, Segarra J, Melena J. The effect of topical diltiazem on ocular hypertension induced by water loading in rabbits. *Gen Pharmacol* 1999; 32:201-205.
39. Yoshida K, Tanihara H, Hiroi K, Honda Y. Prognostic factors for hypotensive effects of isopropyl unoprostone in eyes with primary open-angle glaucoma. *Jpn J Ophthalmol* 1998; 42(5):417-23.

The invention claimed is:

1. A method of treating an eye disorder characterized by increased intraocular pressure (IOP) comprising:

topically administering to the corneal surface of the eye of a human patient in need thereof, a composition comprising SYL040012 at a dose of between 0.3 mg and 0.9 mg per day; wherein said dose reduces the IOP of the patient by at least 20% compared with the IOP of the patient prior to the administration of SYL040012 and provides a sustained decrease in IOP that lasts for longer than 24 hours after administration of SYL040012.

2. The method of claim 1 wherein SYL040012 is delivered in a volume of between about 30 µl and about 40 µl.

3. The method of claim 1 wherein SYL040012 is delivered to the eye with an eyedropper.

4. The method of claim 1 wherein the IOP of the patient is reduced by between about 25% and about 30% compared with the IOP of the patient prior to the administration of SYL040012.

5. The method of claim 1 wherein decreased IOP persists for at least 2 days.

6. The method of claim 1 wherein the eye disorder is selected from the group consisting of open angle glaucoma, angle closure glaucoma and congenital glaucoma.

7. The method of claim 1, wherein the dose of SYL040012 is administered daily to the corneal surface of the eye of the patient.

8. The method of claim 1, wherein the decrease in IOP is sustained without daily administration of SYL040012.

9. The method of claim 1, wherein decreased IOP persists for at least 4 days following administration of SYL040012.

10. The method of claim 1, wherein the dosage is between 0.3 mg and 0.6 mg per day.

11. The method of claim 10, wherein the dosage is 0.3 mg per day.

* * * * *

SEQUENCE LISTING

```
<160> NUMBER OF SEQ ID NOS: 7

<210> SEQ ID NO 1
<211> LENGTH: 19
<212> TYPE: RNA
<213> ORGANISM: Homo sapiens

<400> SEQUENCE: 1
cauugugcau gugauccag                                                  19

<210> SEQ ID NO 2
<211> LENGTH: 21
<212> TYPE: RNA
<213> ORGANISM: Artificial Sequence
<220> FEATURE:
<223> OTHER INFORMATION: SYL040012 - short Interfering nucleic acid
      (siNA)
<220> FEATURE:
<221> NAME/KEY: misc_feature
<222> LOCATION: (1)..(21)
<223> OTHER INFORMATION: SEQ ID NO: 2 represents the sense strand of a
      double stranded molecule
<220> FEATURE:
<221> NAME/KEY: misc_feature
<222> LOCATION: (20)..(21)
<223> OTHER INFORMATION: deoxythymidine at positions 20 and 21

<400> SEQUENCE: 2
cauugugcau gugauccagn n                                               21

<210> SEQ ID NO 3
<211> LENGTH: 19
<212> TYPE: RNA
<213> ORGANISM: Artificial Sequence
<220> FEATURE:
<223> OTHER INFORMATION: short interfering nucelic acid
<220> FEATURE:
<221> NAME/KEY: misc_feature
<222> LOCATION: (1)..(19)
<223> OTHER INFORMATION: SEQ ID NO: 3 represents the sense strand of a
      double stranded molecule

<400> SEQUENCE: 3
```

```
cauugugcau gugauccag                                              19

<210> SEQ ID NO 4
<211> LENGTH: 19
<212> TYPE: RNA
<213> ORGANISM: Artificial Sequence
<220> FEATURE:
<223> OTHER INFORMATION: short interfering nucleic acid
<220> FEATURE:
<221> NAME/KEY: misc_feature
<222> LOCATION: (1)..(19)
<223> OTHER INFORMATION: SEQ ID NO: 4 represents the sense strand of a
      double stranded

<400> SEQUENCE: 4
cauugugcau gugauccag                                              19

<210> SEQ ID NO 5
<211> LENGTH: 21
<212> TYPE: RNA
<213> ORGANISM: Artificial Sequence
<220> FEATURE:
<223> OTHER INFORMATION: short interfering nucleic acid
<220> FEATURE:
<221> NAME/KEY: misc_feature
<222> LOCATION: (1)..(21)
<223> OTHER INFORMATION: SEQ ID NO: 5 represents the sense strand of a
      double stranded molecule
<220> FEATURE:
<221> NAME/KEY: misc_feature
<222> LOCATION: (20)..(21)
<223> OTHER INFORMATION: deoxythymidine at positions 20 and 21

<400> SEQUENCE: 5
cauugugcau gugauccagn n                                           21

<210> SEQ ID NO 6
<211> LENGTH: 21
<212> TYPE: RNA
<213> ORGANISM: Artificial Sequence
<220> FEATURE:
<223> OTHER INFORMATION: short interfering nucleic acid
<220> FEATURE:
<221> NAME/KEY: misc_feature
<222> LOCATION: (1)..(21)
<223> OTHER INFORMATION: SEQ ID NO: 6 represents the sense strand of a
      double stranded
<220> FEATURE:
<221> NAME/KEY: misc_feature
<222> LOCATION: (20)..(21)
<223> OTHER INFORMATION: deoxyuridine at positions 20 and 21

<400> SEQUENCE: 6
cauugugcau gugauccagn n                                           21

<210> SEQ ID NO 7
<211> LENGTH: 21
<212> TYPE: DNA
<213> ORGANISM: Aequorea victoria

<400> SEQUENCE: 7
ggctacgtcc aggagcgcac c                                           21
```